United States Patent [19]

Sackner

[11] Patent Number: 5,178,151
[45] Date of Patent: Jan. 12, 1993

[54] SYSTEM FOR NON-INVASIVE DETECTION OF CHANGES OF CARDIAC VOLUMES AND AORTIC PULSES

[76] Inventor: Marvin A. Sackner, 300 W. Rivo Alto Dr., Miami Beach, Fla. 33139

[21] Appl. No.: 759,862
[22] Filed: Sep. 16, 1991

Related U.S. Application Data

[63] Continuation of Ser. No. 326,159, Mar. 20, 1989, abandoned, which is a continuation-in-part of Ser. No. 183,773, Apr. 20, 1988, abandoned.

[51] Int. Cl.⁵ .............................................. A61B 5/29
[52] U.S. Cl. ...................................... 128/672; 128/713
[58] Field of Search ............................... 128/671–672, 128/694, 695, 721, 687, 713–719, 774

[56] References Cited

U.S. PATENT DOCUMENTS

| | | | |
|---|---|---|---|
| 3,908,639 | 9/1975 | McIntyre | 128/695 |
| 4,232,682 | 11/1980 | Veth | 128/671 |
| 4,308,870 | 1/1982 | Arkans | 128/671 |
| 4,373,534 | 2/1983 | Watson | 128/721 |
| 4,418,700 | 12/1983 | Warner | 128/694 |
| 4,452,252 | 6/1984 | Sackner | 128/671 |
| 4,456,015 | 6/1984 | Sackner | 128/721 |
| 4,494,553 | 1/1985 | Sciarra et al. | 128/671 |
| 4,576,179 | 3/1986 | Manns et al. | 128/671 |
| 4,674,518 | 6/1987 | Salo | 128/695 |
| 4,815,473 | 3/1989 | Watson | 128/721 |

OTHER PUBLICATIONS

Luisada, A.: The internal pneumocardiogram, Am. Heart J. 23: 676–691, 1942.
Lee, G. de J. and A. B. Dubois: Pulmonary capillary blood flow in man, J. Clin. Invest. 34: 1380–1390, 1955.
Wasserman, K. and J. R. Comroe, Jr.: A method for estimating pulmonary capillary blood flow in man, J. Clin. Invest. 41: 401–410, 1962.
Weiner D. A., C. McCabe, G. Dagostino, S. Cutler, and T. J. Ryan: "Cardiokymography During Exercise Testing: A New Device for the Detection of Coronary Artery Disease and Left Ventricular Wall Motion Abnormalities", Am. J. Card., 51: 1307–1311, 1983.
Chapman, C. B., Baker, Mitchell, Collier: Experiences with a cinefluorographic method for measuring ventricular volume Am. J. Card. 18: 25–30, 1966.
Blair, H. A. and A. M. Wedd: The measurement in man by a pneumocardiographic method of the excess of arterial outflow from the chest over venous inflow during the heart cycle, Am. Heart. J. 17: 541, 1939.
Weiner, D. A.: "Accuracy of Cardiokymography During Exercise Testing: Results of a Multi–Center Study," JACC vol. 6, No. 3, Sep. 1985 502–509.
Davila, J. C.: Symposium on measurement of left ventricular volume Part I, Am. J. Card. 18: 1, 1966.
Eddleman, E. E., Jr., K. Willis, T. J. Reeves and T. R. Harrison: The Kinetocardiogram, I. Method of Recording Precordial Movements Circulation 8: 269–275, 1953.
Eddleman E. E. Jr., K. Willis, L. Christianson, J. R., Pierce, and R. P. Walker: The kinetocardiogram, II, The normal configuration and amplitude, Circulation 8: 370–380, 1953.
Eddleman, E. E. Jr., and K. Willis: The Kinetocardiogram III, The distribution of forces over the anterior chest, Cir. 8: 569–577.
Bosman, A. R. and G. De J. Lee: The effects of cardiac action upon lung gas volume Clin. Sci. 28: 311–324, 1965.
Kazamias, T. M., M. P. Gander, J. Ross, Jr., and E. Braunwald: Detection of Left–Ventricular Wall Motion Disorders in Coronary Artery Disease by Radarkymography, New. Eng. J. Med. 285: 63–71, 1971.

Primary Examiner—Kyle L. Howell
Assistant Examiner—J. Jastrzab
Attorney, Agent, or Firm—Cohen, Pontani, Lieberman & Pavane

[57] ABSTRACT

A method and an apparatus therefor for monitoring cardiac function in an animal or human subject including the steps of: placing a first movement detecting transducer on the torso, said transducer overlying at least part of two diametrically opposed borders of the heart or great vessels; generating a signal indicative of the movement of the torso portion subtended by the transducer, said signal including a cardiac component comprising at least a segmental ventricular volume waveform or a segmental aortic pressure pulse waveform; and assessing cardiac function by monitoring changes in said venticular volume waveform or said aortic pressure pulse waveform.

60 Claims, 21 Drawing Sheets

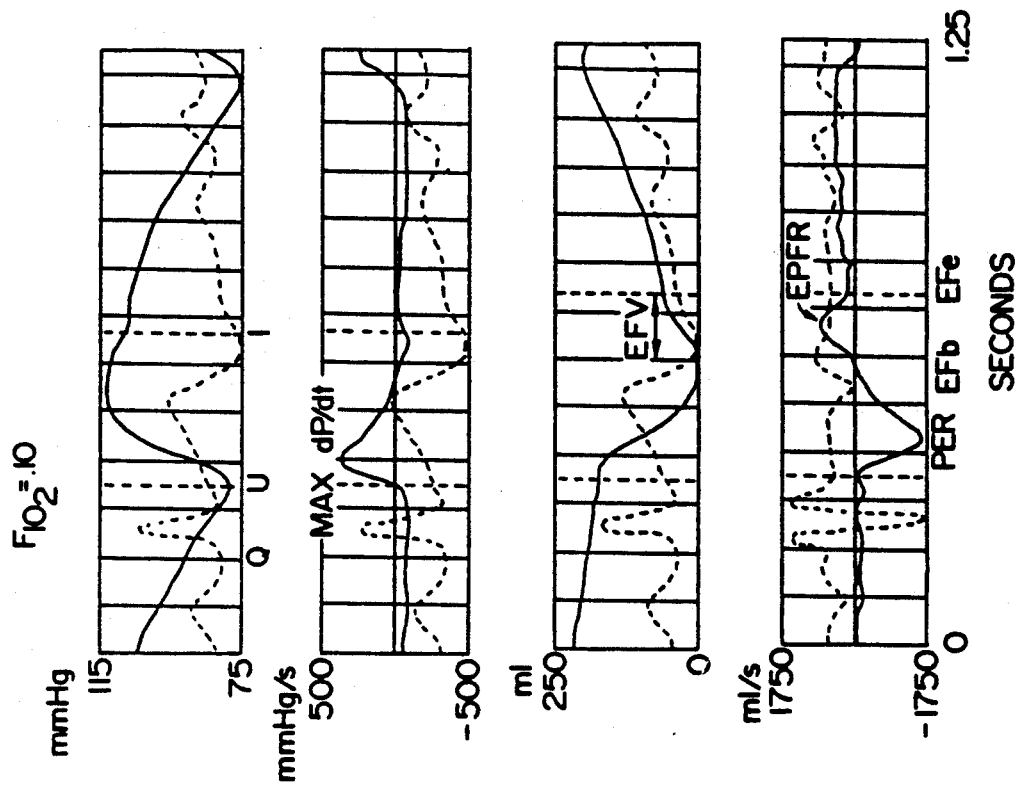
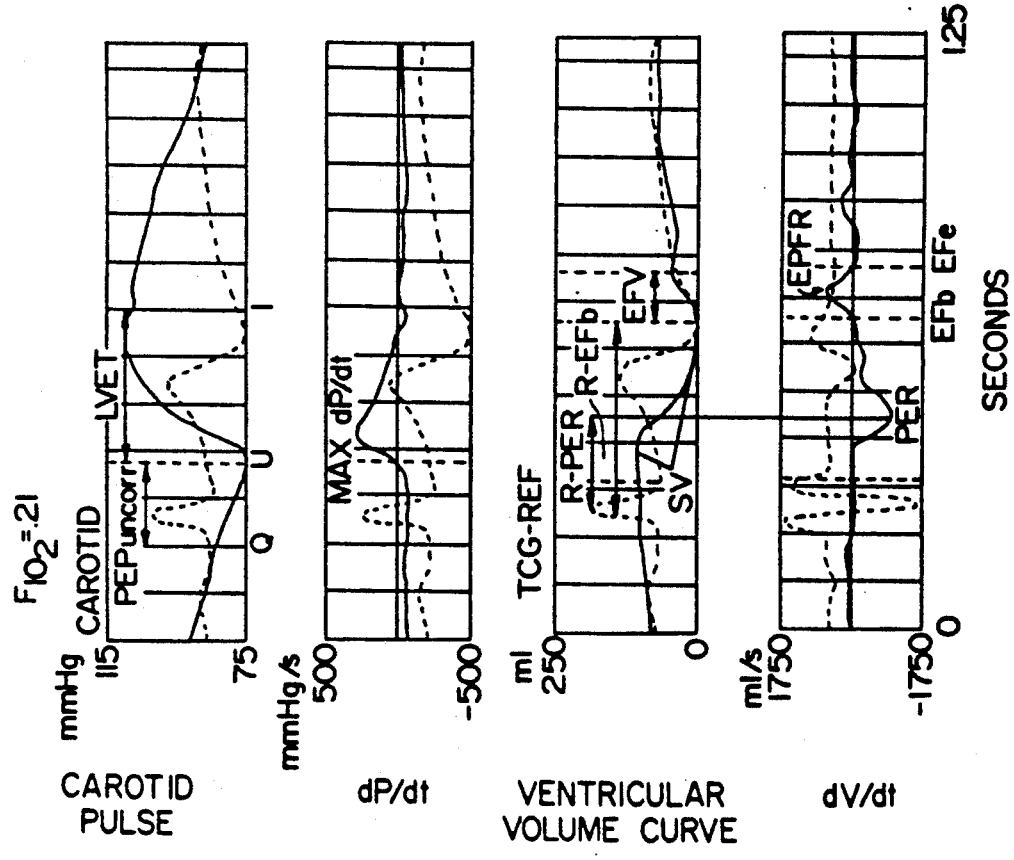
FIG. 22B
FIG. 22A
CAROTID PULSE
dP/dt
VENTRICULAR VOLUME CURVE
dV/dt

SYSTEM FOR NON-INVASIVE DETECTION OF CHANGES OF CARDIAC VOLUMES AND AORTIC PULSES

This is a continuation of U.S. application Ser. No. 07/326,159, filed Mar. 20, 1989, now abandoned, which is a CIP of Ser. No. 07/183,773 filed Apr. 20, 1988, now abandoned.

BACKGROUND OF THE INVENTION

1. Field of the Invention

This invention pertains to non-invasive monitors, and more particularly to non-invasive monitoring of cardiac function.

2. Prior Art

Although the electrocardiogram (EKG) has been the primary non-invasive device for continuously monitoring activity of the heart in clinical medicine, it reflects solely electrical activation of cardiac muscle and provides no information on the mechanical characteristics of the cardiac pump. Consequently, the EKG may show normal or near normal waveforms in the presence of greatly impaired blood pumping capacity of the heart. Conversely, the EKG waveform may be abnormal despite normal or near normal pumping action. In terms of life support, adequate circulation of blood from the heart to the tissues, as reflected by the blood pumping capacity of the heart, is of paramount importance.

Obviously, non-invasive techniques for monitoring the blood pumping capacity of the heart are preferred over invasive ones. Nevertheless, invasive cardiac monitoring techniques, because of their perceived greater accuracy and ability to provide continuous monitoring, continue to be employed in, for example, critically ill patients. Invasive techniques generally have as their basis a catheter, such as a Swan-Ganz catheter, placed such that its tip lays within the pulmonary artery. This provides continuous recording of pressures in the pulmonary artery, and in certain instances pressures in the right ventricle, right atrium and indirectly the left atrium (pulmonary capillary wedge pressure). Injection of inert dye or cold saline from the catheter allows discrete measurements of cardiac output by dye dilution method or thermodilution, respectively. Alternatively, sampling blood for oxygen content in the pulmonary artery and a systemic artery together with measurement of oxygen consumption permits calculation of cardiac output by the Fick principle.

However, insertion of a cardiac catheter into the body may be hazardous. Its use can lead to death, which occurs in 1% of cases, and morbidity, which occurs in 33% of cases, as a result of infection and/or damage to the heart valves, cardiac arrhythmias, and pulmonary thromboembolism. Errors of technique, measurement, judgment and interpretation are common. It has been estimated that one-half million Swan-Ganz catheters used in the United States in 1986 resulted in the death of as many as 1000 or more patients. Furthermore, cardiac catheters cannot be kept in place for more than a few days owing to hazards from infection. They are also costly and laborintensive since catheterized patients require intensive care units which cost two to five times more than standard semi-private beds. In addition, health care workers face the risk of AIDS acquired virus and hepatitis virus as a result of exposure to blood of the infected patient during catheter introduction and subsequent maintenance.

Moreover, cardiac catheters do not directly provide measurement of change in ventricular volume. While such measurements can be indirectly obtained in conjunction with injection of radiopaque dye and roentgenographic imaging, this technique is time-consuming and costly, and dangerous hypotension and bradycardia may be induced by the dye. Furthermore, the number of studies in a given patient is limited by the hazards of x-ray exposure and radiopaque dye injections.

Angiographic techniques provide the most widely accepted means for measuring ventricular volumes. They allow calculation of the extent and velocity of wall shortening and of regional abnormalities of wall motion. When they are combined with measurement of pressure, both ventricular compliance and afterload (i.e., the forces acting within the wall that oppose shortening) can be determined. When the results are expressed in units corrected for muscle length or circumferences of the ventricle, comparisons can be made between individuals with widely differing heart sizes.

Cineangiography provides a large number of sequential observations per unit of time, typically 30 to 60 frames per second. Although contrast material can be injected into the pulmonary artery and left atrium, the left ventricle is outlined more clearly when dye is directly injected into the ventricular cavity. Therefore, the latter approach is used in most patients, except in those with severe aortic regurgitation in whom the contrast material may be injected into the aorta, with the resultant reflux of contrast material outlining the left ventricular cavity.

Injection of a contrast agent does not produce hemodynamic changes (except for premature beats) until approximately the sixth beat after injection. The hyperosmolarity produced by the contrast agent increases the blood volume, which begins to raise preload and heart rate within 30 seconds of the injection, an effect that may persist for as long as two hours. Therefore, this technique cannot be utilized for repetitive measurements within a short time span. Further, contrast agents also depress contractility directly, though newer non-ionic agents have been found useful for minimizing these adverse effects.

In calculating ventricular volumes or dimensions from angiograms, it is essential to take into account and apply appropriate correction factors for magnification as well as distortion produced by nonparallel x-ray beams. In order to apply these correction factors, care must be taken to determine accurately the tube-to-patient and tube-to-film distances. Correction is best accomplished by filming a calibrated grid at the position of the ventricle. Thus, angiographic methods do not have wide clinical application owing to their complexity, safety considerations, invasiveness, and side effects of the contrast agents.

The importance of measuring changes of ventricular volume was well expressed by Davila in a symposium on measurement of left ventricular volume. He pointed out that the description of the functional mechanics of the left ventricle requires measurement of force, strain and velocity (rate of strain). Pressure, a standard measurement in cardiac catheterization laboratories, critical care units and operating rooms, is not necessarily dependent on shape (geometry) or size (volume) of the ventricle. However, force and strain must be expressed in relation to geometry and size of the fluid container.

In the same symposium, Chapman et al described a cineangiographic method for measuring ventricular volume. These workers also took into account the shortcomings of their method and made the following observations: "The ideal system for following change in ventricular volume is obviously one which is fully applicable to the free-living organism, which requires no injection of any sort, and which can be used repeatedly over long periods of time without danger or discomfort to the subject. Such a system, if it ever becomes available, can hardly be based on roentgenologic principles. But until some entirely different principle emerges and is applied, the roentgenologic principle is indispensable." A further requirement for an ideal system would be a minimum of physician or technician time for utilizing such technology and interpreting the results.

Because of the obvious advantage of non-invasive techniques over invasive ones, a continuing search has been made for reliable non-invasive methods of assessing cardiac performance. Such methods are needed particularly in detecting serial changes in cardiac function and in evaluating both acute and chronic effects of interventions such as drug therapy and cardiac operations. The five principal non-invasive methods for assessing cardiac performance are: systolic time intervals, M-mode and two-dimensional echocardiography, radionuclide angiography, gated computerized tomography (CT scanning), and gated magnetic resonance imaging (MRI). All but the first of these are alternatives to angiography for measurement of ventricular volumes and/or dimensions and therefore permit the non-invasive estimation of ejection phase indices. Other than in patients with obstruction to left ventricular outflow, wall stress (afterload) can be estimated from a combination of systemic arterial pressure, ventricular radius, and wall thickness. All four non-invasive imaging methods allow estimation of ventricular systolic and diastolic volumes; none, however, is satisfactory for continuous or near-continuous monitoring of critically ill patients.

Systolic time intervals have been usually obtained with the combination of an external transducer on the carotid artery in the neck to display its pulsations, a microphone over the heart to record heart sounds, and the electrocardiogram. This technique has never enjoyed wide popularity because of both technical and physiologic reasons: (1) reliable, reproducible recordings are difficult to obtain, (2) prominent internal jugular venous pulsations in the horizontal body posture may be superimposed on the carotid artery pulsations rendering interpretation of the carotid arterial waveform difficult, (3) accurate recording of heart sounds may be difficult to obtain particularly in patients with obesity or emphysema, (4) systolic time intervals are sensitive to many pharmacologic and hemodynamic influences including changes in left ventricular preload and afterload which may introduce misleading values, (5) changes in duration of systolic time intervals can be influenced by patient posture and time of day when recordings are made, (6) carotid pulse contours to calculate systolic time intervals can be difficult to interpret in patients with aortic valve disease, and (7) presence of congestive heart failure can either normalize abnormal values or make normal values abnormal.

Echocardiography involves ultrasonic imaging of ventricular wall motion to monitor cardiac function. With this technique, the dynamics of ventricular wall contraction and the internal dimensions of the cardiac chambers can be recorded. The apparatuses used for echocardiography encompass a wide variety of increasingly sophisticated and computer-aided imaging and analysis systems. The transducer placements on the chest require the services of skilled technicians and incorrect placements lead to misleading information. Furthermore, these systems are quite expensive, not readily portable, require that the patient be studied in the left lateral decubitus posture, and are not intended for continuous monitoring of critically ill patients throughout the day or during exercise.

In addition to the foregoing drawbacks, echocardiography has several inherent limitations. For example, all ultrasonic beams have a defined breadth and height comparable to the size of the crystal transducer face. Beyond its focal point, the beam's cross-sectional area enlarges in direct proportion to the distance from the transducer face. Therefore, in M-mode (single transducer) echocardiography, two laterally separated structures may appear in direct anteroposterior relationship.

Two-dimensional electrocardiographic techniques also produce distortions, which increase with increasing distance between the target and the central beam axis. In these instruments, axial resolution (1-2 mm) is superior to lateral resolution (4-5 mm). Because of the complex nature by which two-dimensional images are generated, artifacts may appear as intracardiac masses to the casual observer. Further, delineation of the endocardium of the left ventricle in its entirety is achieved only 70 to 80% of the time. Also, respiratory interference limits the ability to obtain continuous beat to beat recordings, particularly during exercise.

Attempts have also been made to determine left ventricular end-diastolic and end-systolic volumes from dimensions derived from echocardiography. These have met with variable success, depending on the patient population studied and whether m-mode or two dimensional echo techniques were employed. M-mode dimensions are used to calculate left ventricular volume through an application of the angiographic concept of the left ventricle as an ellipsoid. However, M-mode echocardiography allows measurement of only one left ventricular dimension, the septalposterolateral dimension, which is viewed at the level of the chordae tendineae. Consequently, to calculate volume from this single dimension, the following assumptions are made: (1) the ventricle being examined does in fact approximate the geometry of an ellipsoid, both in diastole and systole; (2) the septal-posterolateral dimension measured coincides with the minor axis of the ellipsoid; (3) the orthogonal minor axis is equal to the measured minor axis; and (4) the major axis is twice the length of the minor axes. While good correlations between angiographic and echo left ventricular volumes have been obtained, correlations are poor in patients who have asynergetic ventricular wall motion, which occurs in patients with coronary artery disease in whom damaged areas of the left ventricular wall do not move in phase with the normal areas. Also, because ventricular volume curves as a function of time cannot be derived without utilization of several assumptions and approximations, they are not usually reported.

Two-dimensional echocardiography offers considerable advantage for estimation of left ventricular volume because it allows direct measurement of all three hemiaxes on the ellipsoid model and also allows application of other volume formulations, such as Simpson's rule. Studies have shown that correlations between echocardiographic and angiographic volumes are substantially improved when two-dimensional methods are used, and good correlations have been obtained even in the presence of ventricular asynergy. The greatest disadvantage to quantitative two-dimensional echocardiography is the inability to obtain technically satisfactory images in all patients and the labor involved in analyzing the studies. This technique, as with the M-mode, does not readily provide dynamic changes of ventricular volume over time.

Echocardiography has also been employed to estimate the velocity of ventricular circumferential fiber shortening (Vcf). This echo measurement is analogous to the derivative of change in ventricular volume during systole and serves as a measure of ventricular contractility. Its application in M-mode echocardiography assumes that the left ventricular internal dimension is measured at the midventricular level. The mean rate of shortening is determined by dividing the calculated circumference expression by the left ventricular ejection time (ET), which may be measured from the concomitant carotid pulse tracing or from the time duration of echocardiographic aortic valve opening. Peak Vcf can be similarly derived by extrapolation from the maximum systolic slope of posterior and septal walls. Vcf is inaccurate in patients with asynergetic movement of the left ventricle as in patients with ischemic heart disease.

Mean velocity of circumferential fiber shortening ($V_{cf}$) can be determined simply from measurements of end-diastolic and end-systolic dimensions by echocardiography, CT scanning, or MRI. Since the ventricle is approximately circular at its minor axis the circumference is equal to diameter (D). Mean $V_{cf}$ (in circumference/sec) is therefore the difference between end-diastolic and end-systolic circumference (in cm) divided by the product of the duration of ejection (in sec) and the end-diastolic circumference. Values of $V_{cf}$ obtained by echocardiography compare closely with those determined from cineangiograms.

Echocardiography has also been employed to estimate stroke volume (SV), which is the difference between end-diastolic volume and end-systolic volume. This technique suffers from the inherent lack of accuracy in volume estimations and, clinically, stroke volume varies widely with different physiologic circumstances such as body size, heart rate, posture and exercise. It is, therefore, not as useful a measurement as contractility. Nevertheless, provided that subjects with left ventricular asynergy are excluded from analysis, fair correlations have been reported between stroke volume derived from M-mode echocardiographic and two dimensional echo techniques on the one hand, and both thermodilution and angiographic stroke volume measurements on the other.

Another non-invasive technique is the apex cardiogram which is obtained by employing a transducer over the maximal cardiac impulse on the anterior surface of the left hemithorax in combination with the electrocardiogram. This technique is of limited usefulness for several reasons. In particular, the recording of the apex cardiogram is strongly affected by the characteristics of the recording transducer and coupling of the transducer to the skin surface. In the absence of a palpable cardiac impulse on the chest, which may occur in patients with emphysema, the apex cardiogram cannot be obtained. Moreover, interpretation of the apex cardiogram waveform for heodynamic measurements is even more problematic than systolic time intervals.

Another non-invasive device for monitoring cardiac function in the kinetocardiograph. This device records localized chest wall movements with a transducer consisting of a small metal arm attached to a flat end piece which directly contacts the chest wall. Motion of the metal arm is transmitted to a bellows, connected to a piezoelectric or strain gauge transducer.

The bellows and pickup are mounted from a crossbar over the bed, and the end piece can be placed perpendicular to any location on the chest. The amplified signal, denoted the kinetocardiogram (KCG), is obtained during breath holding at end-expiration. The KCG measures low frequency inward and outward chest movements, which range from 5 microns in the left axilla to 200 microns directly over the precordium.

Kinetocardiography differs from apex cardiography in which outward movements are accentuated by an air displacement funnel transducer placed over the apex of the heart (a position where pulsations can be felt by the examiner). For example, the KCG senses true displacements of the precordium because of its external crossbar frame of reference, whereas the apex cardiogram senses relative rib cage interspace motion. Also, the KCG is sufficiently sensitive so that records can be obtained from many points over the precordium and not just at the apex as with the apex cardiograph.

KCG recordings in humans were initially described in locations where the precordial electrocardiographic electrode leads were conventionally positioned. In these locations, the KCG generally depicts inward motion of the chest wall following the QRS wave of the electrocardiogram followed by a large number of low frequency vibrations superimposed upon an upward, outward motion. The investigators who initially described the KCG attributed the chest movements to a combination of the following factors: (1) movements due to the cardiac impact against the chest wall, (2) changes in the intrathoracic blood volume as the result of ejection or filling of the heart, (3) impact of blood in the great vessels against the chest wall and (4) positional and shape changes of the contracting and relaxing heart. Tracings of KCG over the anterior and posterior rib cage reveal: (1) a carotojugular type of pulse tracing in the infraclavicular area (attributed by the investigators to a mixed arterial venous pulse transmitted from the subclavian or axillary blood vessels), (2) with the subject prone, a waveform configuration similar posteriorly to the $V_4$ electrocardiographic electrode placement position, and (3) with upright posture, a smaller amplitude, noisy opposite deflection signal at a posterior position corresponding to the anterior KCG signal. The investigators attributed these findings to a combination of the factors listed above.

The KCG depicts precordial outward systolic bulges in approximately 66% of patients with known myocardial infarctions. The largest outward motion is found most often at the $V_3$ electrocardiographic electrode placement position. Outward precordial bulges occur during exercise in about 30% of patients who develop anginal pain.

Although the KCG appears to provide useful information on the mechanical properties of heart muscle, it has never received widespread clinical acceptance. This is probably because of: (1) the unwieldy transducer to patient interface; (2) restriction of patient movement and need for breathholding during recording; (3) noisy, often uninterpretable signals; (4) requirement of a great deal of skill to interpret recordings from different locations on the rib cage; and (5) lack of quantitation of the KCG waveforms with respect to changes of ventricular volume events obtained from analysis of the recordings.

Another non-invasive device for monitoring cardiac function is the cardiokymograph (CKG). This device, available from Cardiokinetics, Seattle, Wash., consists of a circular, flat capacitive plate mounted in a plastic ring strapped to the chest. Tissue motion beneath the transducer distorts an induced electromagnetic field which in turn alters the frequency of the oscillator plate. This change of frequency is converted to a change of voltage proportional to the chest wall motion at the transducer site and then displayed as an analog waveform. The CKG provides waveforms during breath-holding quite similar in appearance to the kinetocardiogram. It depicts left ventricular wall motion abnormalities just like the KCG and therefore can be used to improve the diagnostic accuracy of exercise testing as an additional marker of myocardial ischemia.

The cardiokymogram suffers from the same limitations as the kinetocardiogram, namely, (1) an unwieldy transducer to patient interface; (2) restriction of patient movement and need for breathholding during recording; (3) noisy, often uninterpretable signals; (4) requirement of a great deal of skill to interpret recordings from different locations on the rib cage; and (5) lack of quantitation of the CKG waveforms with respect to changes of ventricular volume events obtained from analysis of the recordings.

Electrokymography and radarkymography are still other techniques for non-invasively monitoring cardiac function. The motions of the borders of the cardiovascular shadow obtained with roentgen rays can be visualized directly on a fluoroscope by using a photomultiplier tube to give a phasic analog signal from cyclic variations in light produced by movement of the underlying heart border (electrokymography), or from a video monitor of the fluoroscopic image and similar tracking technology (radarkymography). A graphic record of the segmental motion on the left heart border provides recordings which closely resemble the contour curve of changes in left ventricular volume over time.

Such technology can be utilized to diagnose localized segmental dysfunction of the ventricular wall. For example, radarkymography has been used to diagnose ventricular wall abnormalities, including asynergistic and akinetic motion, associated with acute myocardial infarction. Radarkymography compares favorably with left ventricular cineangiography in the diagnosis of asynergistic myocardial contraction.

However, radarkymography and electrokymography can be used only where an interface is visualized between the cardiac silhouette and adjacent structures. Poor visualization is encountered in pulmonary fibrosis, pulmonary edema, pleural fibrosis and bony distortions of the rib cage. Dyspneic patients are difficult to study since extraneous motions of the heart caused by respiration introduce artifacts. Finally, both methods subject the patient to exposure to Roentgen rays and this hazard prevents their use in situations requiring long term monitoring.

A still further non-invasive technique for monitoring cardiac function is impedance cardiography. It has long been recognized that the passage of a high frequency, low electrical current signal between electrodes placed on the heart or directed through the heart across the intact thorax produces changes of electrical impedance which varies directly with the length and inversely with the cross-sectional area of the conductor.

In impedance cardiography, detection of localized motion of the heart is highly dependent upon the placement of the electrodes. To circumvent the problems of electrode placement, the entire thorax is treated as a conductor by placing exciting and receiving electrodes at the upper and lower borders of the thorax. This permits estimation of the magnitude of cardiac stroke volume as the difference in impedance between systole and diastole. Absolute values of cardiac stroke volume (amount of blood ejected by the heart per beat) are obtained by incorporating the rate of change of impedance (an index of the velocity differences in pulse volume) into an empirically derived equation. It is the derivative waveform of torso impedance that forms the basis for its measurement by the commercial device, the Minnesota impedance cardiograph, for calculating cardiac output.

Although impedance cardiograms were initially recorded during breathholding to eliminate impedance changes superimposed by respiration, it has been found that ensemble-averaging of torso impedance waveforms using the R-wave of the electrocardiogram as a trigger pulse provides comparable waveforms during normal respiration in healthy subjects at rest and exercise and in critically ill patients.

Because changes of transthoracic electrical impedance to detect changes of cardiac volume are highly dependent on electrode placement, segmental changes of cardiac volumes and accurate reproduction of volume contours over time cannot readily be recorded with such technology. On the other hand, treating all changes of hemodynamics of the entie thorax as a single conductor appears to provide reasonable estimates of stroke volume of the heart.

It has also long been recognized that heart motion produces gas flow within the lungs, though the mechanism of this phenomenon has puzzled investigators for many years. One of the earliest researchers suggested that each heart contraction sent a volume of blood out of the thorax and the consequent negative pressure inside the affectivity rigid container caused an inflow at the mouth. Although this "aspirating" effect of the heart was subsequently well documented, the observation that the flow pulses were also present in open-chest animal preparations pointed to other mechanisms.

Cardiogenic flow pulses have been attributed to direct beating of the heart against the pulmonary parenchyma. Although artifactually induced vascular pressure pulses produce flow oscillations in the airways, these oscillations can still be seen in an airway of a lobe to which the lobar branch of the pulmonary artery has been entirely obstructed. Furthermore, injection of 25-50 ml of saline into the canine pericardial sac markedly diminishes all cardiogenic oscillations within intrapulmonary conducting airways despite the presence of normal pulmonary arterial pulsations. These observations suggest that neither pulmonary vascular pulsations nor volume changes of the heart, which should not be affected by a small pericardial effusion, were responsible for cardiogenic flow oscillations.

The heart has an irregular shape and contracts with a twisting action; this results in a forceful thrust to some parts of the adjoining lung, whereas other parts follow the inward movement of the myocardium. It is these localized transient inflations and deflations which appear to produce intrapulmonary to-and-fro flow oscillations. Pericardial fluid tends to make the external surface of the pericardial sac more spherical so that rotation or twisting of the heart no longer produces a thrust against the lung, thereby diminishing cardiogenic oscillations of the air columns.

The actual redistribution of the flow pulse among intrapulmonary airways originating from the heart depends upon relative impedance of the airways. Its magnitude depends upon the force and acceleration of the cardiac movement. However, apart from the heart movement, intrapulmonary factors must also influence the pattern and extent of transmission of the pressure impulse and the zonal volume changes that it causes. Thus, whether a zone adjacent to the heart deflates or not, giving rise to a flow pulse in the airways subtending it, depends upon its time constant. The smaller its compliance and resistance, the more likely it is to respond to the cardiogenic pressure impulse by emptying. In contrast, if the time constant is high (e.g., due to increased airway resistance), minimal emptying occurs during the time of the pressure cycle, resulting in smaller or absent flow pulses in the airways.

The preceding discussion accounts for a number of experimental observations regarding recordings of expired gas flow. Thus, although cardiogenic oscillations appear on recordings of continuous expired gas concentrations in most normal subjects, patients with emphysema may not demonstrate this phenomenon. Absence of cardiogenic oscillations has been observed in patients with bronchial asthma, with oscillations reappearing after partial relief of the bronchial obstruction. Lung disease oscillations are not seen in the trachea unless they are also present within the lobar airways.

Luisada in 1942 reviewed the historical background for the designation, "pneumocardiogram", and defined it as the recording of pressure changes which occur in the air passages of the lung as a consequence of the heart beat. He noted that graphic recordings of this phenomenon were published as early as 1861 in animals and in humans in 1876. He utilized a pressure sensing transducer from one nostril while the subject breathed normally and employed electronic filtering to eliminate the slower respiratory waves. He attributed the four positive and five negative deflections of the resulting complex waveform to the following events: 1) auricular contraction; 2) papillary muscle contraction; 3) first ventricular wave; 4) peripheral pulse; 5) second ventricular wave; 6) semilunar valve closure; 7) first diastolic wave; 8) tricuspid valve opening; and 9) second diastolic wave. He believed that the multiple waveforms present in the pneumocardiogram were due to the difference between venous inflow to, and arterial outflow from, the thorax.

Blair and Wedd in 1939 measured rib cage movements from a site below the sternum by recording pressure changes within a bellows pneumograph manufactured by the Harvard Apparatus Company. The cardiogenic oscillations recorded during breathholding were attributed by the authors to excessive outflow of blood from the chest over inflow into the chest. They calculated this volume to be 30 ml by assuming that the recording below the sternum was representative of the entire thorax.

Cardiogenic oscillations during breathholding have also been observed on analog signals from devices which display the total external movements of the respiratory system. Such oscillations were noted by Lee and Dubois in 1955 who enclosed a subject within an airtight chamber, the body plethysmograph. The subject first breathheld after inspiring air and small oscillations of pressure (calibrated as a volume) were sensed from the body plethysmograph with a sensitive pressure gauge. These oscillations were attributed to the heartbeat, but no significance was attached to the resulting complex waveforms by Lee and Dubois or by the present inventor. After the recording was obtained while breathholding on air, the subject inspired nitrous oxide ($N_2O$), a soluble gas, which was taken up by the pulmonary capillary blood flow.

In 1961, Wasserman and Comroe modified the body plethysmographic technique of Lee and Dubois by substituting the subject's own thorax for the rigid body plethysmograph. Change in spirometric volume then reflected the exchange of gas molecules between alveoli and blood as long as thoracic volume remained constant. The latter was an important requirement of the method. Accordingly, to continuously monitor any movements of the chest or abdomen which would invalidate this requirement, two mercury in rubber strain gauges were placed around the rib cage and upper abdomen and connected together to permit analog recording of circumferential movements of the combined rib cage and abdominal compartments.

Wasserman and Comroe believed that the cardiogenic oscillations observed with their method reflected changes in thoracic blood volume. They did not consider the oscillations to be related to changes in ventricular volume. The present inventor accepted the interpretation given by Wasserman and Comroe to the cardiogenic oscillations observed with their technique and used Wasserman and Comroe's results in a review paper on measurement of cardiac output by alveolar gas exchange.

In 1965, Bosman and Lee utilized a body plethysmograph-flowmeter method "to study the effects of cardiac contraction upon changes in lung gas volumes during breathholding both with the glottis open and closed." They reported and depicted curves with multiple rises and falls from the body plethysmograph and pneumotachograph. They interpreted these complex waveforms as showing an excess of aortic outflow over venous inflow to the thorax during systole and a reverse during diastole. Using more sophisticated technology, their work confirmed the findings of Blair and Wedd.

SUMMARY OF THE INVENTION

The present invention, which is sometimes referred to herein as the thoracocardiograph or TCG, is based upon the discovery that during breathholding, small oscillations detected by sensors placed on the rib cage (RC) and abdominal (AB) surfaces and ordinarily used to monitor breathing patterns closely resemble ventricular volume curves and aortic pressure pulses depending upon their respective placements on these surfaces. These sensors include those which measures changes of rib cage and abdominal dimensions, such as the respiratory inductive plethysmograph which measures changes in cross-sectional area; the inductance circumferential transducer which measures partial cross-sectional area; the mercury in silastic strain gauge, bellows pneumograph, and differential linear transformer which measure circumference and partial circumference; magnetometers which measure diameters; and partitioned pressure, volume and capacitance body plethysmographs which measure volumes.

BRIEF DESCRIPTION OF THE DRAWINGS

In the drawings:

FIGS. 22A and 22B compare waveforms measured during breathing of room air (left panel) and an hypoxic mixture (right panel).

DETAILED DESCRIPTION OF THE PREFERRED EMBODIMENTS

I have discovered that during breathholding, cardiogenic oscillations derived from sensors placed on the rib cage and abdomen surfaces for displaying breathing movements differ in waveform configuration depending upon the location enclosed by the vertical height of the sensor. The invention will be particularly described with reference to the respiratory inductive plethysmograph and its associated sensors, though as noted above, the present invention may be practiced with other devices used for measuring dimensional changes at the rib cage and abdomen.

The respiratory inductive plethysmograph is commercially available from Non-Invasive Monitoring Systems, Inc. (NIMS) under the trade names Respigraph and Respitrak and is described in U.S. Pat. No. 4,308,872, the entire content of which is incorporated herein by reference. Basically, this apparatus comprises two coils of Teflon-insulated wire sewn onto elastic cloth bands encircling the rib cage and abdomen. The leads from the wires are connected to LC oscillator modules, or preferably a shared module, such that the inductance of the wires comprises the inductance element of the oscillator. Changes in the cross-sectional area of the rib cage and abdominal compartments result in changes in the inductance of the wires and hence changes in the oscillation frequency of the oscillator. The resulting signals for the rib cage and abdominal compartments are demodulated and displayed as analog voltage signals. In respiration applications, these signals can be calibrated and summed to reflect absolute tidal volume.

Figure 1B:
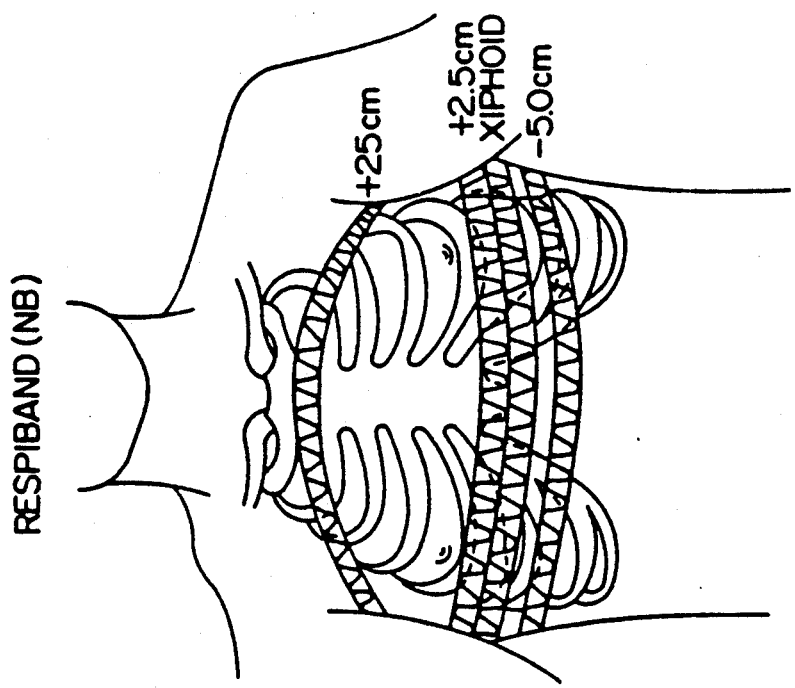
FIGS. 1A and 1B are diagrammatic representations showing the placement of wide band (left panel) and narrow band (right panel) transducers about the human torso.
Figure 1A:
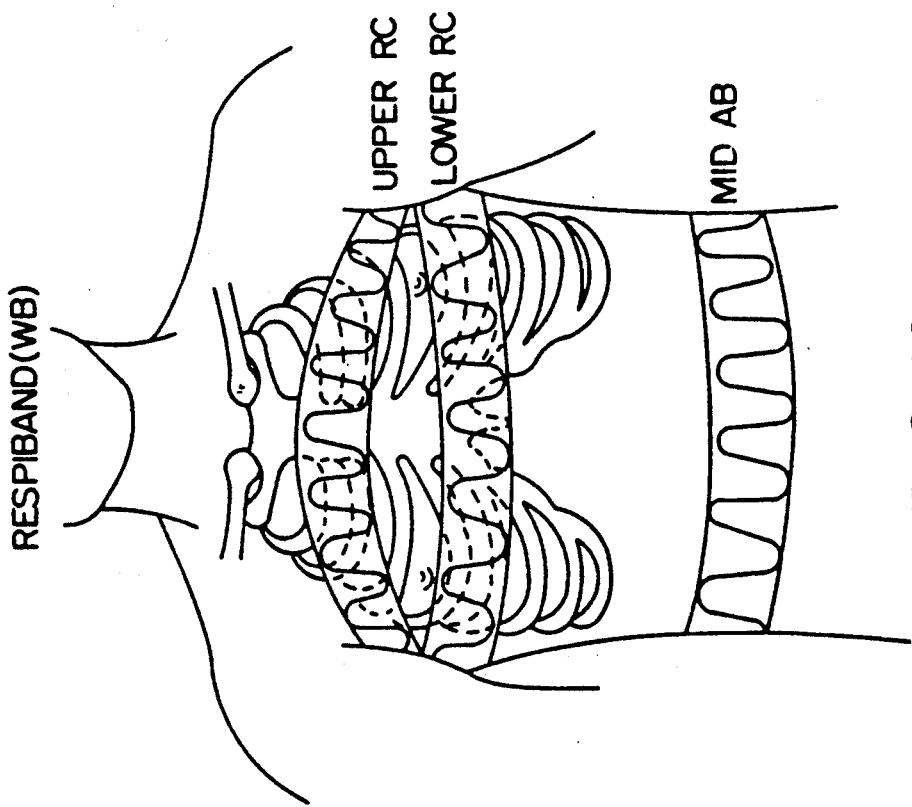

FIG. 1 shows placements of sensors employed with the respiratory inductive plethysmograph. The left-hand panel in FIG. 1 illustrates the placement of commercially available wide band (WB) sensors, 10 cm in height, on the upper and lower rib cage (RC) and mid-abdomen (AB). In the usual application of this device to non-invasively monitor breathing patterns, the sensor shown at the upper rib cage closely depicts the placement for respiratory monitoring.

For purposes of the present invention, the respiratory inductive plethysmograph was used with modified sensors. In particular, sensors as employed in the present invention were only 2.5 cm in height, such that each sensor subtended a narrower portion of the torso than the commercial wide band sensors shown in the left-hand panel in FIG. 1. The narrow band (NB) sensors used with the present invention are shown in the right-hand panel in FIG. 1. The xiphoid process of the sternum has been taken as the arbitrary point of reference for placement for the NB sensors employed with the present invention, as it is an easily recognized anatomic location which demarcates the caudal limit of the bony thoracic cage in the midline from the cranial limit of the soft tissues of the abdomen. While the invention will be described herein in conjunction with the NB sensors, it will be apparent as this description progresses that sensors of any height may be employed, depending upon the information being sought.

Figure 2:
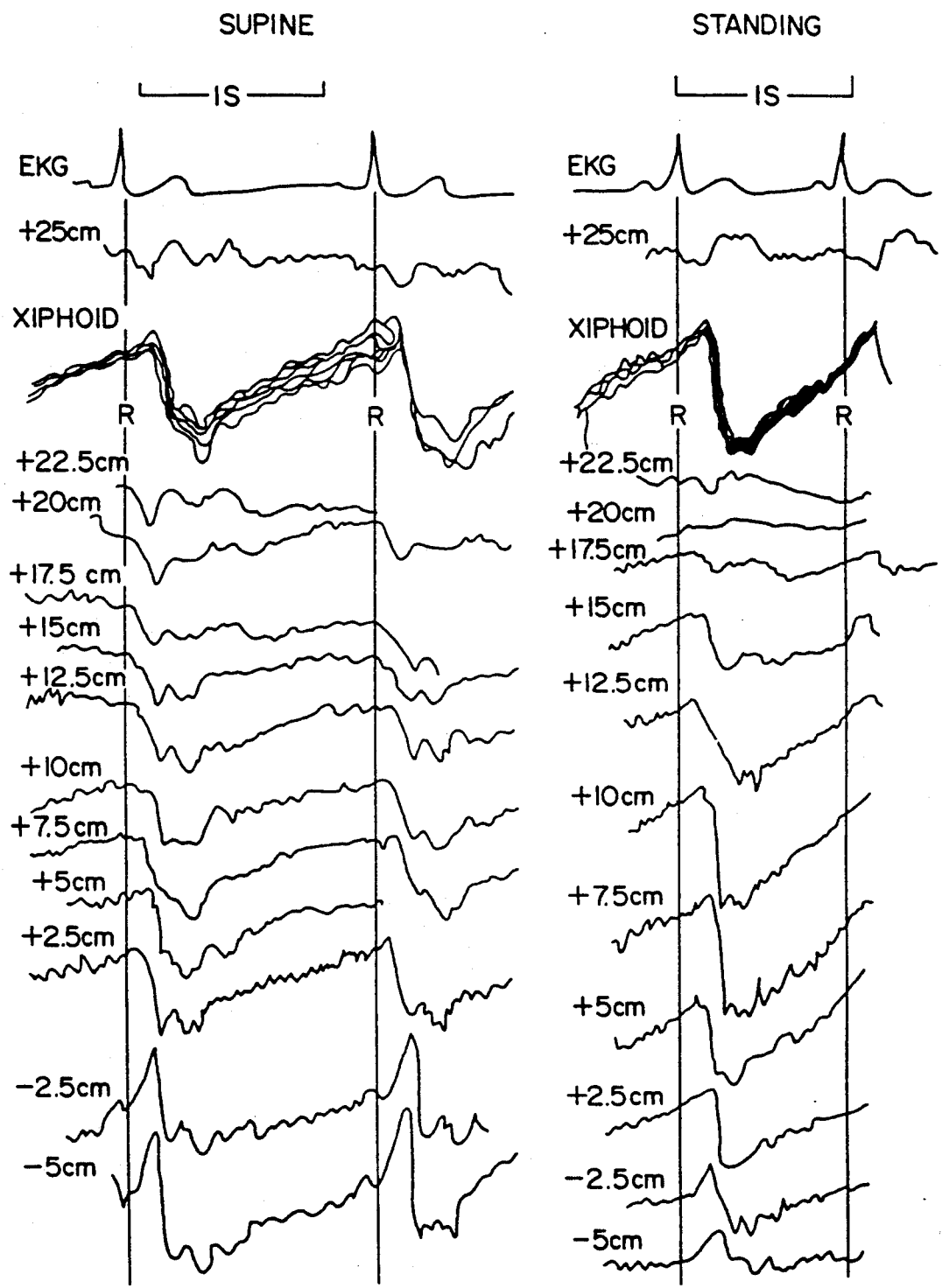
FIG. 2 is a graphic representation showing waveforms derived in accordance with the present invention in the supine (left panel) and standing (right panel) postures.

FIG. 2 shows, for a normal adult, waveforms traced from polygraph recordings of the electrocardiogram (EKG) and the analog voltage signal from a narrow band sensor employed with a respiratory inductive plethysmograph as taken during sequential breathholds. The QRS complex of the EKG, labeled R in FIG. 2, marks electrical activation of the ventricles of the heart, which precedes ventricular muscular contraction. As is well known, contraction of the ventricle causes ventricular volume to decrease as blood is ejected (systole) from the ventricles into the thoracic aorta and pulmonary artery.

As indicated in FIG. 2, a single narrow band sensor was moved either above or below the xiphoid process at 2.5 cm intervals before each sequential breathhold. As also indicated in FIG. 2, the trial was repeated in both the supine and standing positions, left and right-hand panels in FIG. 2, respectively. The uppermost cranial border of the rib cage in a normal adult 187 cm in height, whose waveforms are depicted in FIG. 2, was situated +25 cm above the xiphoid process. The multiple tracings at the xiphoid process denote repetitive tracings of sequential breathholds from polygraph recordings at this site and demonstrate good reproducibility of the measurement. Of course, the tracings at the xiphoid process were taken with a narrow band sensor disposed between the "−2.5 cm" and "+2.5 cm" positions, i.e. over the xiphoid process, the xiphoid process tracings being shown between the "+22.5 cm" and "+25 cm" in FIG. 2 simply as a matter of convenience.

By making the recordings during breathholding, waveform deflections due to respiration are eliminated. Accordingly, it is known that the waveforms depicted in FIG. 2 are due to physiological changes unrelated to breathing. Because the changes in rib cage and abdominal dimensions reflected by the signals shown in FIG. 2 are of considerably lower amplitude than those resulting from respiration, the gain of the respiratory inductive plethysmograph employed in generating the waveforms, the Respigraph, was adjusted to about ten to twenty times the gain setting for respiration applications.

The narrow band sensors were placed such that recordings were ultimately obtained from almost all horizontal cross-sectional regions of the rib cage surface in the supine and standing postures. The configurations of the resulting waveforms as depicted in FIG. 2, which I have found to be related to specific cardiovascular structures, distinctly differed depending upon the cross-sectional location subtended by the band. Thus, the cardiogenic signals from bands disposed at the level of the xiphoid process show a rapid decrease in volume (systole) following the R wave of the EKG, which reached its nadir shortly before or after termination of the T wave of the EKG, depending upon the precise location of the band. As shown, the diastolic phase of ventricular muscular relaxation is marked, at the xiphoid process, by a brief initial rapid increase in ventricular volume to a more gradual rise before reaching a peak plateau coincident with the next R wave. This plateau continues slightly past the R wave before the downstroke of systole repeats itself.

The configurations of the cardiogenic oscillations shown in FIG. 2 are, as shown, extremely dependent upon location of the sensor both in the supine and standing postures. The waveforms taken at the xiphoid as depicted in FIG. 2 closely resemble the ventricular volume waveform as measured by sensors of length, diameter or volume surgically installed on the hearts of dogs, or from a cardiometer enclosing the isolated heart.

Still referring to FIG. 2, the band placed +25 cm above the xiphoid, i.e. at the uppermost portion of the sternum, depicts an upgoing deflection following the R wave rather than a downgoing deflection as detected at the xiphoid process. It more closely resembles the waveform of the descending aortic pressure pulse as detected in the prior art using other techniques. From +2.5 to +17.5 cm above the xiphoid, the amplitudes of the signals in the supine posture diminish but still resemble ventricular volume curves. There are less marked variations of amplitude in the standing posture. For example, the amplitude of the waveform recorded with a band placed +10 cm above the xiphoid in the standing position is approximately equivalent in amplitude to the waveform at the xiphoid process. As also seen in FIG. 2, the timing of the systolic downstroke following the R wave and its slope varies among the recordings taken at different locations above the xiphoid.

The waveforms of cardiogenic oscillations in the supine posture show an initial upward systolic deflection at the xiphoid location which is more pronounced −2.5 and −5 cm below the xiphoid. This upward deflection denotes the period of isovolumetric contraction, a well documented phenomenon. At locations below the xiphoid, the mid-anterior sections of the band lie on the abdominal surface but the lateral and posterior sections overly the rib cage. Therefore, changes in left ventricular volume are primarily recorded at these locations because the cardiac apex of the left ventricular wall is located at the lowermost portion of the rib cage. Further, the slope of systolic ejection appears to be steeper at these locations below the xiphoid than above it. This is consistent with prior art observations that apical segments display a higher velocity of contraction than basilar segments.

As is well known, during isovolumetric ventricular contraction immediately after electrical activation of the heart muscle, shortening of the long axis predominates such that the heart becomes more spherical and the transverse diameter toward the apex actually increases. This phenomenon accounts for the brief, often quite prominent, upward systolic deflections of isovolumetric contraction at the xiphoid, −2.5, and −5 cm band locations, and the diminution or absence of an upward deflection at this same point in time in the waveforms in locations from +2.5 to +17.5 cm above the xiphoid. This is consistent with the observation in canines that the isovolumetric contraction of the left ventricle varies in prominence depending upon the location where the dimensional gauges are surgically installed. The circumferential and length waveforms from the canine left ventricle as reported in the literature display prominent isovolumetric contraction which is strikingly similar to the human isovolumetric contraction waveform from bands placed from −2.5 to −10 cm below the xiphoid (See FIGS. 1 and 2). The upward isovolumetric deflections are less marked in the standing posture presumably because greater longitudinal orientation of the heart due to gravity produces a lesser spherical cardiac shape at the onset of systole than in the supine posture.

The timing sequence in FIG. 2 is consistent with fluoroscopic imaging of the heart in which the observer perceives a wave of muscular contraction from the cardiac base to apex. Similar timing of the initial changes in ventricular volume with systole has also been described with dimensions recorded during biplane coronary cineangiograms. FIG. 2 also shows that the amplitude of the change in ventricular volume is less at the cranial than the caudal portions of the rib cage. Since the base of the heart is located more cranially than the apex, the finding of lesser changes of volume is consistent with the conclusion that the band measures the horizontal sector of cardiac volume changes subtended by the height of the band. So, if the atria and ventricles lie anatomically in the same horizontal plane at a particular rib cage location, summation of such signals would be expected. And, indeed, summation of the ventricular and atrial volume curves as reported in the literature is consistent with the waveforms observed at positions+12.5 to+17.5 cm above the xiphoid as shown in FIG. 2. Thus, in these waveforms, the downstroke of systole is more gradual at the base of the heart than the apex because the atria are in their diastolic period and rising in volume thereby cancelling in part the ventricular systolic volume amplitude. Further, at the nadir of ventricular systole, the upward rounded curve represents the predominant peak of atrial diastole.

Figure 3:
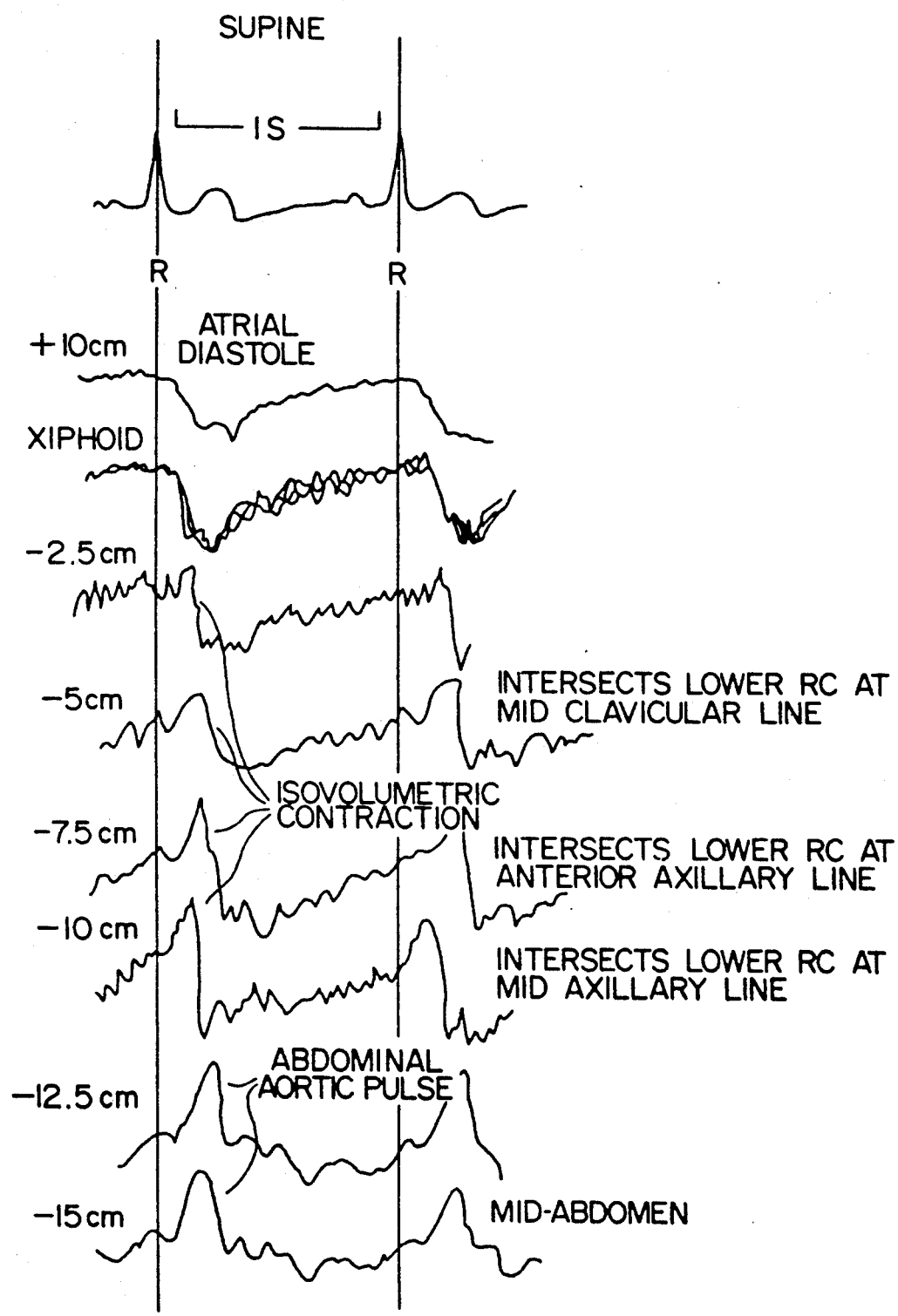
FIG. 3 is a graphic representation similar to the left panel in FIG. 2.

FIG. 3 shows tracings from the bands 2.5 cm in height in the same subject whose waveforms are depicted in FIG. 2, but taken one week later at locations ranging from 15 cm below to 10 cm above the xiphoid process. As seen from a comparison of FIGS. 2 and 3, the appearance of the waveforms is consistent for recordings taken at the same locations, but one week apart, evidencing good reproducibility of the results. Referring to FIG. 3, the bands placed −12.5 cm and −15 cm below the xiphoid on the abdominal surface show deflections more closely resembling the abdominal aortic pressure pulse. It should be noted that the −15 cm location was 2.5 cm above the umbilicus.

Figure 4B:
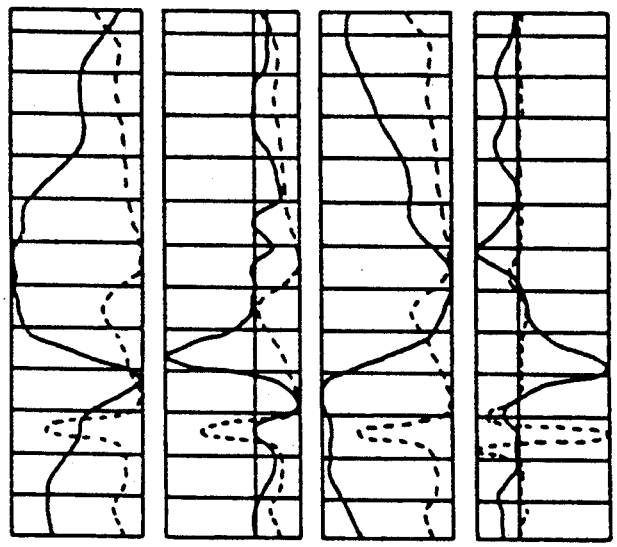
FIGS. 4A and 4B are recordings from a semirecumbent normal subject using ensemble averaging to display an averaged vascular pulse and a ventricular volume curve with their corresponding derivatives.
Figure 4A:
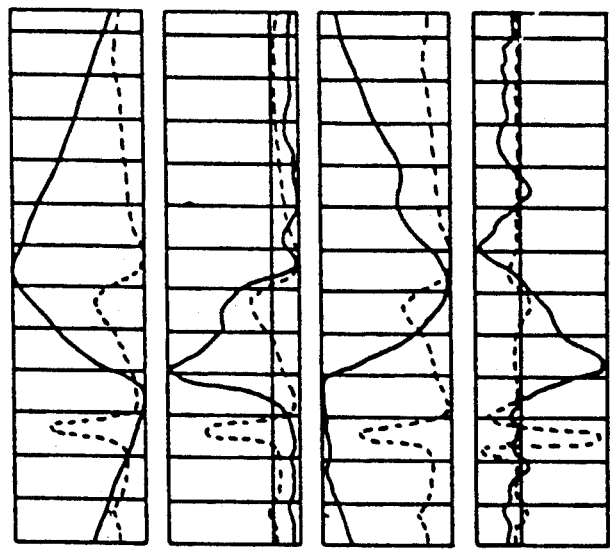

Although the description thus far is based on waveforms generated during breathholding, the display of the averaged waveform at any location can also be obtained during breathing by the well known technique of ensemble-averaging using the R wave of the EKG or the upstroke of a systemic arterial pulse obtained noninvasively or invasively as a trigger to display solely the hemodynamic signals while eliminating the breathing waveform. FIG. 4 shows the ventricular volume curve together with the electrocardiograph and also the descending aortic pressure pulse from the upper rib cage with the electrocardiogram using an average of 50 heart beats. In FIG. 4, starting with the left panel, from top to bottom, the first panel shows the carotid arterial waveform; the second panel shows the carotid arterial waveform derivative; the third panel shows the ventricular volume curve from TCG just below the xiphoid process; and the fourth panel shows the derivative of TCG. On the right, from top to bottom, the first panel shows the descending thoracic aortic pulse obtained from TCG just above nipple level on the RC; the second panel shows its corresponding derivative; and the third and fourth panels show, respectively, the left ventricular volume curve from TCG just below the xiphoid process, and the corresponding derivative. The finding of an aortic pressure pulse on the recordings shown on the right side of this Figure demonstrates heterogenicity of cardiogenic oscillations from different thoracic sites. The hatched line depicts the EKG; the lowest panel displays the second derivative of the EKG.

The preceding description of varied waveform configurations of cardiogenic oscillations obtained with external sensors placed on the rib cage and abdominal surfaces accounts for the inconsistencies and misinterpretations regarding previous recordings of these signals. Thus, the signal from a whole body plethysmograph represents the sum of both positive and negative deflections from the rib cage added to positive deflections from the abdominal compartment. Similar mixing of signals is displayed on the sum signal from the rib cage and abdominal signals utilizing the respiratory inductive plethysmograph or bellows pneumograph in which transducers are placed upon both the rib cage and abdominal surfaces. And in a previous study using a single bellows pneumograph placed just below the sternum, the authors interpreted the waveform assuming that this location was representative of the cardiogenic oscillations of the entire thorax rather than reflecting cardiovascular events localized to their recording site.

Figure 5:
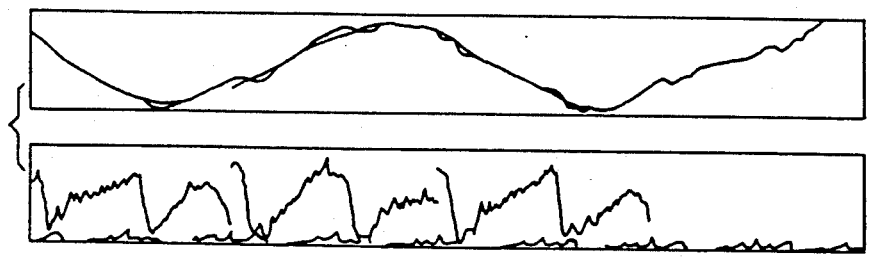
FIG. 5 is a graphic representation showing the use of curve fitting techniques to extract cardiogenic waveforms from raw data derived in accordance with the present invention.

FIG. 5 illustrates a further technique for obtaining waveforms in accordance with the present invention during breathing. Referring to FIG. 5, the irregular waveform in the upper tracing shows the signal detected during breathing from a single narrow band sensor connected to a respiratory inductive plethysmograph, with the band positioned at the xiphoid, which indicates that the band is positioned over the ventricles. This raw signal includes both a larger amplitude respiration component, and a smaller one due to cardiac function, the latter being the one of interest here. To remove the signal component resulting from respiration, the raw signal in the upper tracing of FIG. 5 is matched, using a conventional curve fitting equation with a cubic spline over sequential cycles, each of which comprises two cardiac beats. If this curve fit, depicted as the discontinuous "smooth" waveform in the upper tracing, is subtracted from the raw signal, the tracing depicted in the lower panel results, the discontinuities in the lower tracing resulting from the curve fitting technique described above, though these discontinuities may be eliminated by employing conventional smoothing techniques to adjacent curve fits as will be apparent to those of ordinary skill in the art. Similarly, the "noise" on the lower tracing may be eliminated by high frequency filtering. Even with the discontinuities and noise on the tracing in the lower panel, it may be seen that the lower tracing corresponds to ventricular volume curves as published in the literature. The lowermost tracing in the lower panel is simply the EKG. The removal of the respiratory waveform to provide beat to beat display of the cardiogenic oscillations may also be carried out by other digital adaptive filtering techniques.

Since compliance of the rib cage remains constant during brief recording periods, change in amplitudes of the ventricular volume curve should provide accurate tending of relative changes in stroke volume as well as ventricular contractility and relaxation characteristics. The product of stroke volume and heart rate represents cardiac output and relative trends of the latter are also available. Also, timing of systole and diastole slopes of various portions of the ventricular volume curve, and various volumes as a ratio to stroke volume, should allow comparisons among different subjects and trend plots over time in a single subject. Finally, measurement of the absolute value of stroke volume by independent methods such as dye dilution, thermal dilution, impedance cardiography, radionucleide scans of the heart, 2-D echocardiography, angiography, etc., allows one to set the initial amplifier gains for the external sensor used in the present invention to be equivalent to the values of stroke volume obtained by the preceding methods.

It has not been possible to calibrate the ventricular volume curve to absolute volumes independent of another method for obtaining absolute values of stroke volume. However, it is possible to compare amplitude of cardiogenic oscillations from one site on the rib cage to another at a reference location. Thus, in a series of experiments involving six normal subjects, a band 2.5 cm in height was placed horizontally immediately below the xiphoid process and designated reference (REF) because solely the left ventricle is transected anatomically at this site. Other bands were placed 3 cm below REF, and 3, 6, 9 and 12 cm above REF, and at the umbilical level. The electrical gain of respiratory excursions of these bands was adjusted to be equivalent to the band at REF and the amplitude of their cardiac waveforms was compared to the cardiac waveform of the REF band. In supine, semi-recumbent and seated postures, at REF, 3 cm below and 3 cm above it, the cardiac waveforms had the contour of ventricular volume curves. More cephalad, waveforms tended to have complex oscillations. At the highest rib cage level and umbilicus, waveforms resembled descending aortic-pressure pulses. Amplitudes of waveforms were generally smaller at the +6 and +9 cm sites compared to the REF band in all postures, viz. 41% to 70% of REF ($p<0.01$). There was no correlation between amplitudes of cardiac and corresponding respiratory waveforms ($r= -0.14$). Thus, this method of amplitude analysis should permit a study for obtaining normal values and be capable of diagnosing hypokinetic ventricular segments (decreased motion) as might occur in patients with ischemic heart disease.

As stated earlier, TCG appears to reflect changes in cross-sectional area of the cardiovascular structures underlying the transducer. Since respiratory airflow and regional lung expansion may be altered by different density gases filling the lungs, we investigated whether or not the TCG waveform was influenced by this factor. In addition to TCG for measurement of changes of stroke volume (SV), systolic and diastolic timing and volume events, PEP/LVET was obtained as a carotid systolic time interval (STI). Six normal men breathed (1) air, (2) 20% $O_2$ and 80% He, and (3) 20% $O_2$ and 80% $SF_6$ for 5 minutes and 3 measures of TCG and STI's were carried out over another 5 minutes. There were no differences among the 3 gas mixtures whose densities varied 12-fold, in heart rate, SV, PEP/LVET, peak ejection rate/SV, and time of R-wave to peak ejection rate. Therefore, this confirms that TCG measurement of ventricular function is unaffected by changes in physical composition of gases within the lungs. This is additional evidence that TCG displays changes in volume of underlying cardiovascular structures.

Figure 6:
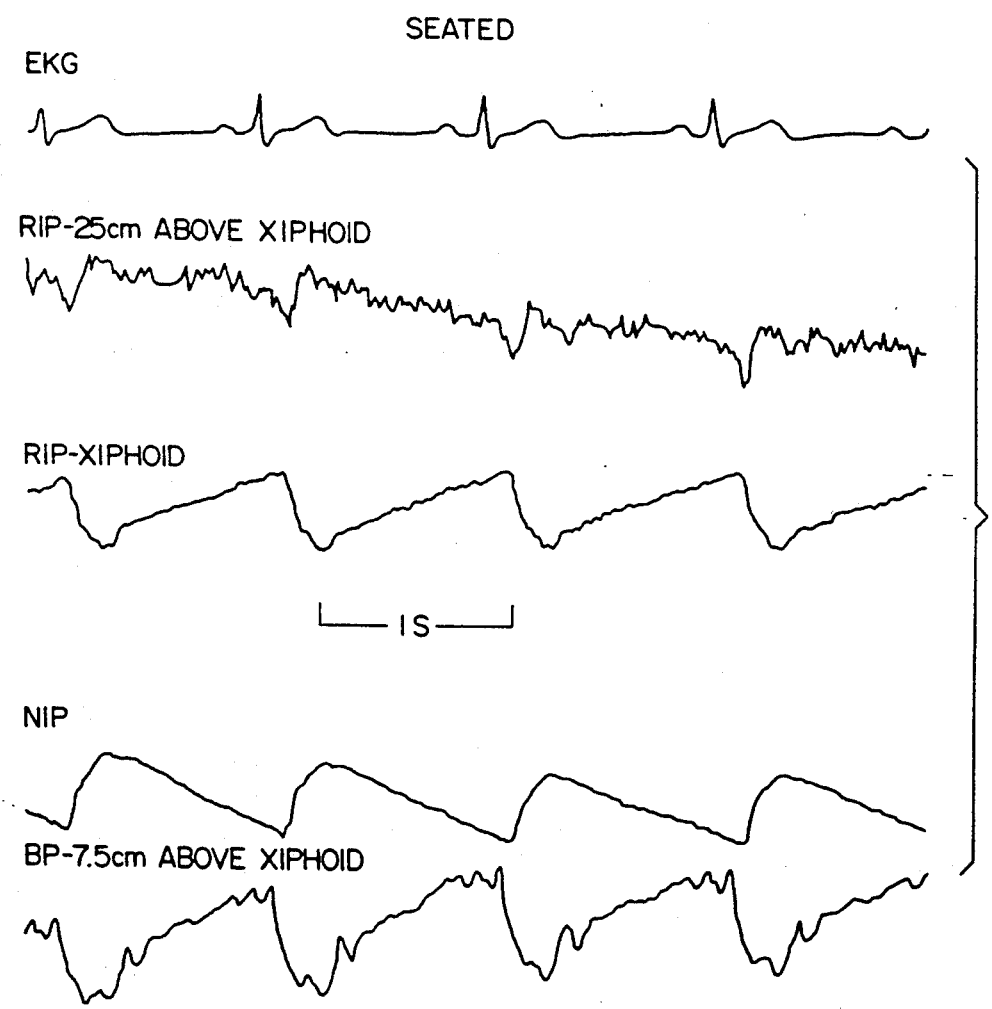
FIG. 6 compares waveforms derived using a narrow band sensor and a single bellows pneumograph.

While the present invention has thus far been described based on measurements taken with a respiratory inductive plethysmograph using narrow and wide bands, other externally placed respiratory monitoring devices can be employed to record changes of cardiac volumes and aortic pressure pulses. FIG. 6 illustrates this point. The waveforms shown in FIG. 6 were obtained by placing narrow bands connected to a respiratory inductive plethysmograph at the xiphoid and +25 cm above it, and a single bellows pneumograph (BP)+7.5 cm above the xiphoid process. NIP denotes the recording from a neck inductive plethysmograph which provides a non-invasive waveform of the carotid arterial pressure pulse as described in U.S. Pat. Nos. 4,452,252 and 4,456,015, the entire contents of which are hereby incorporated herein. The EKG is also shown in FIG. 6. FIG. 6 shows that the waveform from the bellows pneumograph (BP) closely resembles the ventricular volume curve obtained using the respiratory inductive plethysmograph.

Figure 7:
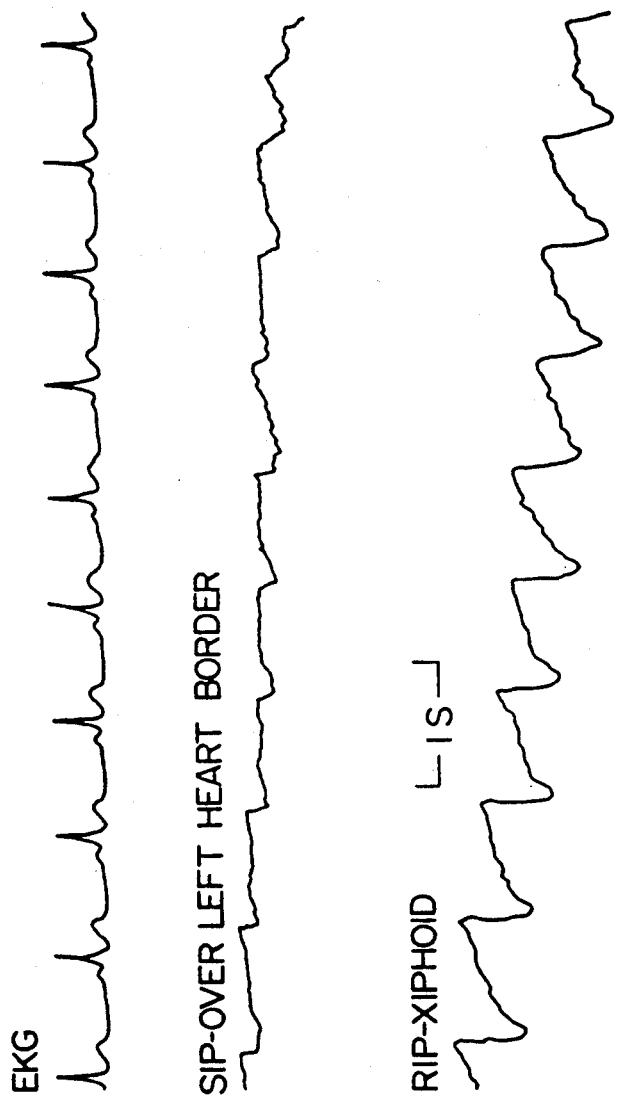
FIG. 7 compares waveforms derived with a narrow band sensor and a surface inductive plethysmograph.

Referring to FIG. 7, a recording taken with a surface inductive plethysmograph (SIP) placed on the rib cage over the left border of the heart is shown together with the EKG and a recording taken with the respiratory inductive plethysmograph at the xiphoid. As described in Canadian Patent No. 1,216,635, the entire content of which is hereby incorporated by reference, the SIP measures changes of surface cross-sectional area underneath the wire loop of the transducer. As seen in FIG. 7, the SIP also provides a recording depicting ventricular volume changes, though the waveform appears slightly distorted compared to the corresponding waveforms obtained from cross-sectional slices around the rib cage as recorded with the respiratory inductive plethysmograph using a band placed at the xiphoid process.

Figure 8:
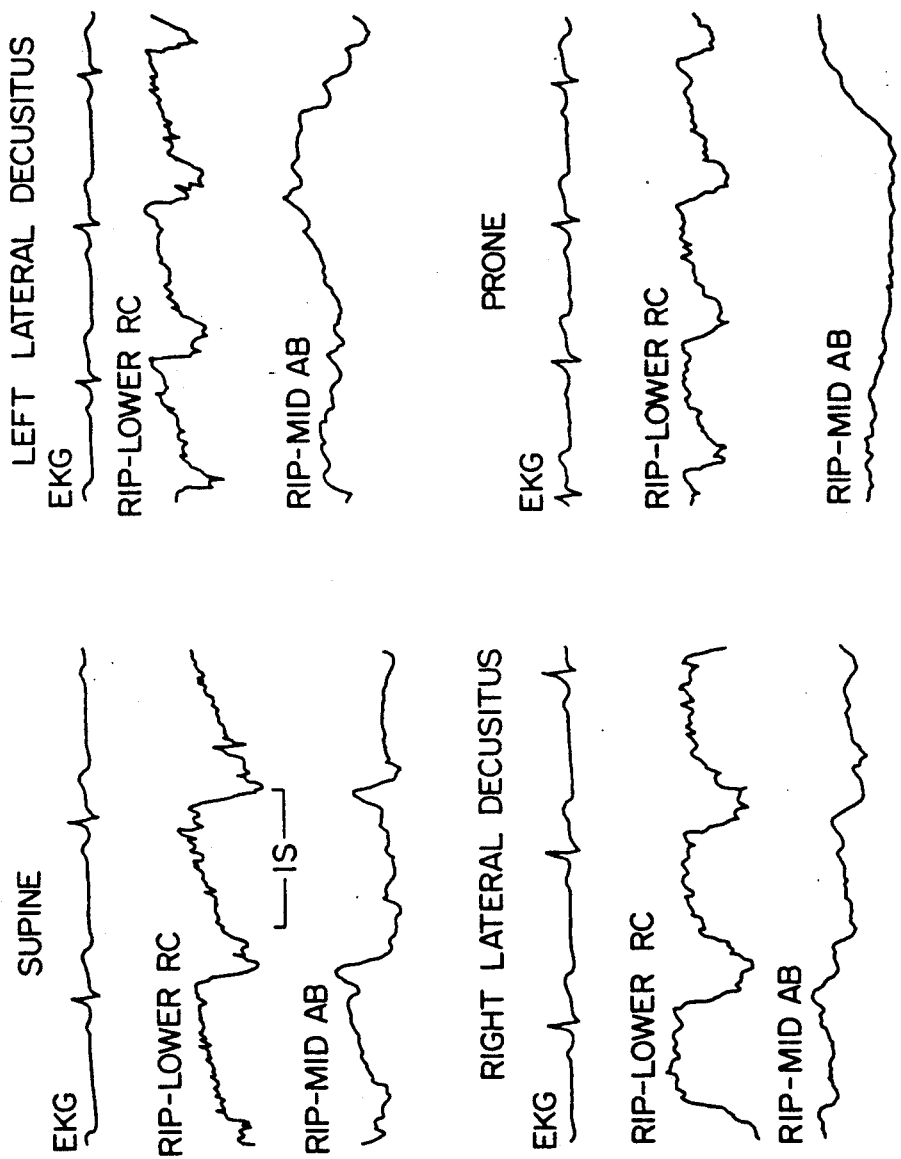
FIG. 8 shows waveforms derived, for different horizontal postures, using a wide band sensor at the lower rib cage and another wide band sensor at the mid-abdominal level.

FIG. 8 depicts, for different horizontal postures, ventricular volume waveforms recorded with a wide band placed at the lower rib cage placement shown in the left panel in FIG. 1, and the abdominal aortic pressure pulse recorded with a wide band placed at the mid-abdominal level shown in FIG. 1. The EKG is also shown in FIG. 8. The ventricular volume curves show similar configurations among the various postures, but there is accentuation of the isovolumetric contraction period of the systolic part of the ventricular volume curve in the left lateral decubitus and the prone postures. Slight alterations in configuration with changes of posture are not unexpected since the heart is free to rotate and elongate in the rib cage as a function of gravity. The sector of the heart subtended by the externally placed band or a similar external monitoring device would change if the heart became oriented in a different plane. The abdominal aortic pressure pulse tracing is clearly recognizable in the supine posture and completely absent in the prone posture. This is probably because the supine posture permits maximum transmission of the aortic pulse through the more compliant anterior abdominal wall whereas in the prone posture, aortic pressure pulse transmissions to the anterior wall are highly damped leaving only the back and the sides of the abdomen for transmission of vascular oscillations and the large amount of muscle mass present in the back and sides of the abdomen causes compliance (increased stiffness) of these regions which damps the aortic pulse pressure waveforms. Since compliance of the entire rib cage is much higher than the heavily muscled lower back, satisfactory recordings of ventricular volume curves are obtained in all horizontal postures.

Devices other than the respiratory inductive plethysmograph which are utilized to measure breathing patterns by changes of partial circumferences are conventionally placed on the anterior surface of the rib cage and abdomen compartments. These include the bellows pneumograph, mercury in silastic strain gauges, and the linear differential transformer. They are incapable of accurately monitoring breathing movements in the prone position because motion of the anterior surface of the transducer on the rib cage is restricted owing to the interposition of the transducer between tissues of the rib cage and the horizontal surface of the bed. Since these devices do not generally provide accurate measures of lateral and posterior motion, they cannot display ventricular volume curves when the subject assumes the prone posture. Magnetometers, which are conventionally placed to measure changes of anteroposterior diameters of the rib cage and abdomen compartments with respiration, do not produce accurate representations of changes of respiration nor ventricular volume when the subject assumes the lateral decubitus postures owing to exclusion of lateral rib cage movements which go undetected by the transducer.

Figure 9:
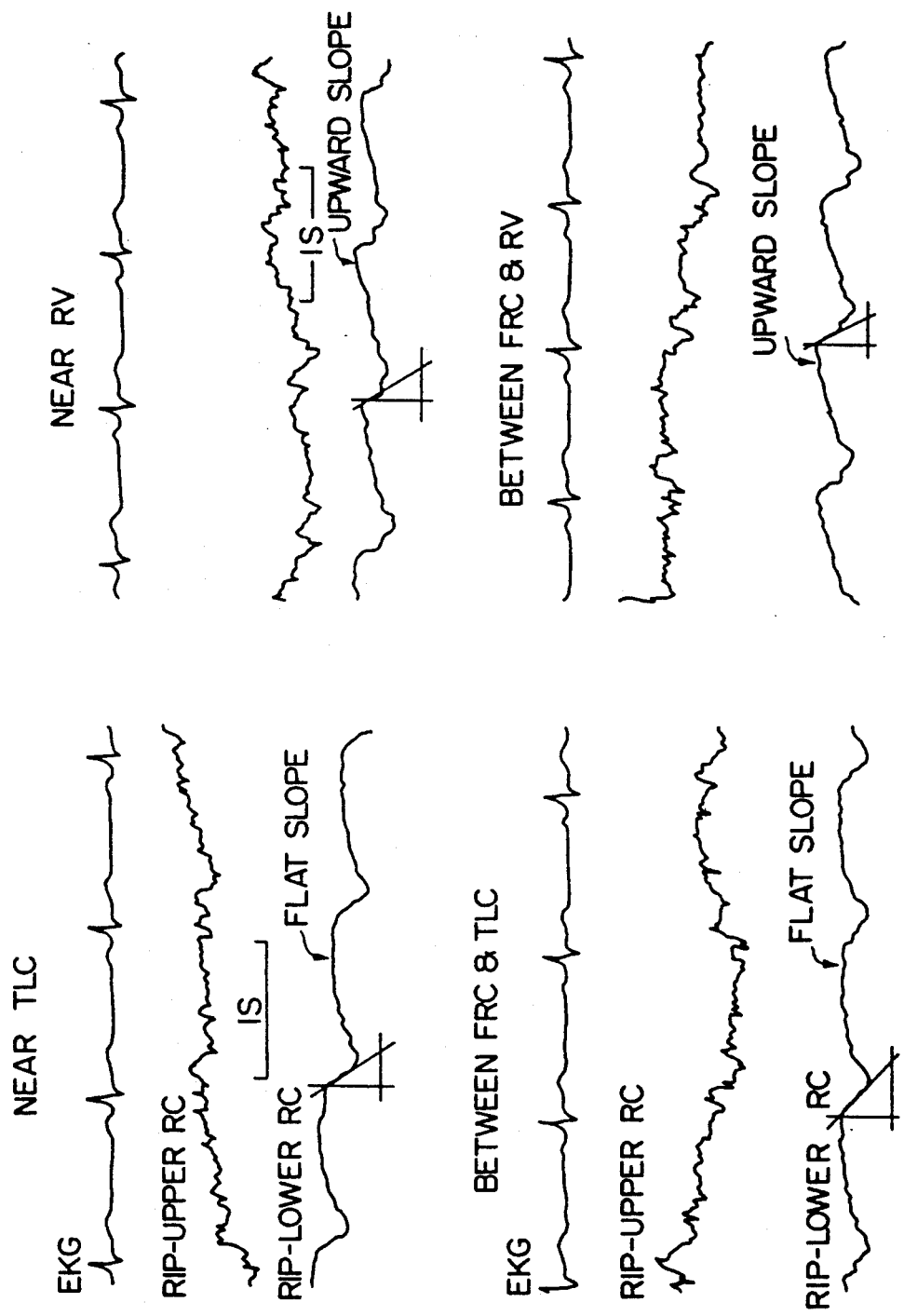
FIG. 9 illustrates waveforms derived using wide band sensors at the upper and lower rib cage placements and showing the effect of lung volume on ventricular volume curves.

FIG. 9 depicts the effect of lung volume on ventricular volume curves obtained in accordance with the present invention. In each of the four panels, recordings taken with a respiratory inductive plethysmograph using a wide band at the upper and lower rib cage placements in the left-hand panel of FIG. 1 are shown together with the EKG. In FIG. 9, near TLC indicates near total lung capacity signifying that the subject inspired a deep breath almost to the limit of vital capacity and breathheld with a closed airway at this lung volume level. FRC signifies functional residual capacity, i.e. lung volume at the end of normal expiration, and "between FRC & TLC" in FIG. 9 signifies a moderately deep inspiration followed by a breathhold at this level. RV connotes residual volume, i.e. lung volume after full expiration, and "near RV" in FIG. 9 indicates breathholding at a lung volume near the lower limits of vital capacity. "Between FRC and RV" signifies breathholding after a moderately deep expiration.

As seen in FIG. 9, the configuration of the diastolic slope of the ventricular volume curve is altered by the lung volume level such that the terminal slope is flat at the high lung volumes and slopes upward at low lung volumes. Furthermore, the slope of initial ventricular systole is more gradual at the high lung volume ("near TLC" and "between FRC & TLC") than the steeper slopes at the low lung volumes ("near RV" and "between FRC & RV"). There are minimal differences in the amplitudes of ventricular volume curves at the various lung volume levels except for a slight increase at the level "between FRC & RV". These data suggest that myocardial contractility is increased during breathholding at low lung volumes compared to high lung volumes as expressed by the more rapid slope of systole at the low lung volume level. Furthermore, the flat slope of the terminal diastolic curve suggests that at the high lung volume levels ventricular compliance is decreased compared to ventricular compliance at the low lung volume levels. In the latter situation, the terminal curve slopes upward. This further suggests that the primary ventricular volume measured by the band at the lower rib cage placement is the left ventricular volume since it is known that both diminished myocardial contractility and lowered left ventricular compliance occur at increasing lung volume levels.

Figure 10:
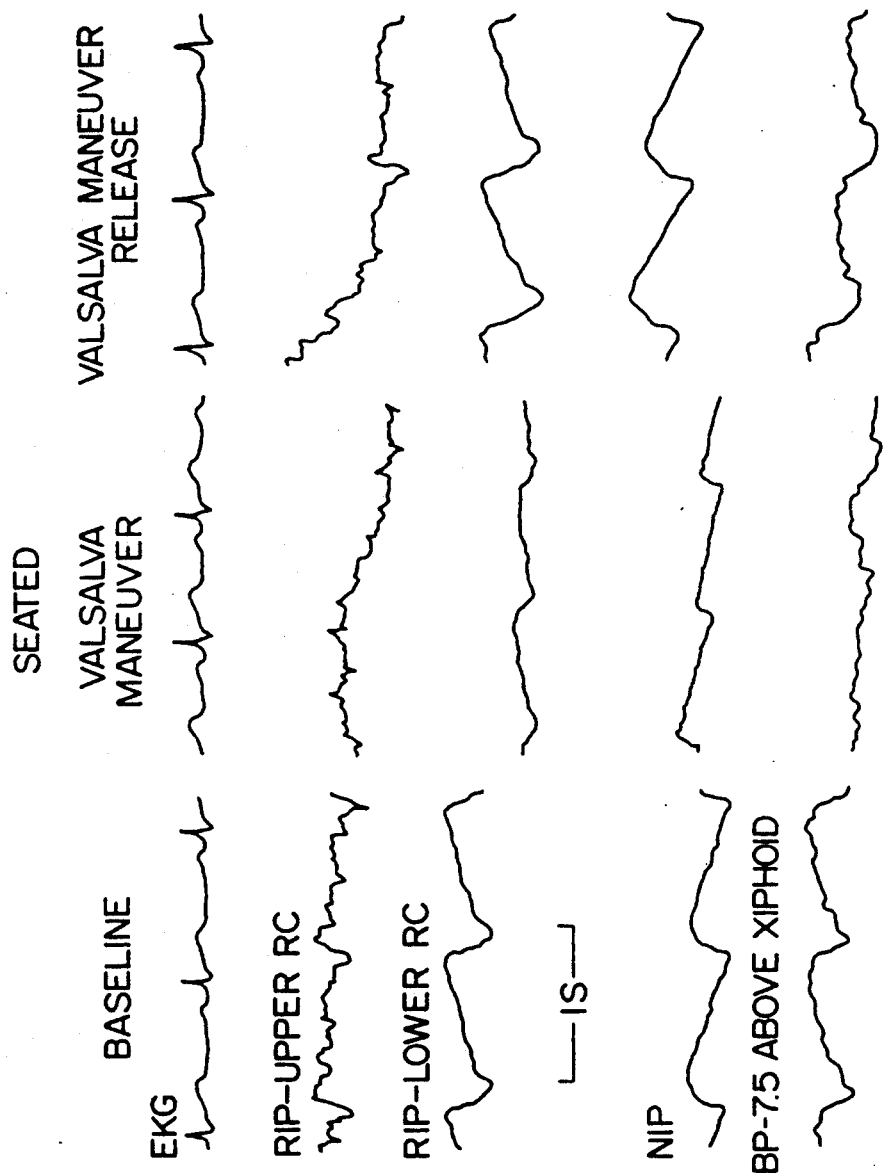
FIG. 10 shows the effect of the Valsalva maneuver on ventricular volume curves derived in accordance with the present invention.

Referring to FIG. 10, the effect of the Valsalva maneuver on ventricular volume curves derived in accordance with the present invention is shown. The Valsalva maneuver consists of straining against either a closed glottis or an occluded airway. FIG. 10 depicts such a maneuver with wide bands placed at the upper and lower rib cage placements depicted in the left-hand panel in FIG. 1. Waveforms derived from the neck inductive plethysmograph (NIP) for recording carotid arterial pressure pulses and the bellows pneumograph (BP) placed +7.5 cm above xiphoid for recording ventricular volume are also displayed, as is the EKG. During the Valsalva maneuver, the pressure at the mouth rose to about 60 cm $H_2O$. The amplitudes of the ventricular volume waveform at the lower rib cage placement and the thoracic aortic pressure pulse at the upper rib cage placement showed a marked fall in amplitude during the Valsalva maneuver, as did the NIP and BP recordings. The slope of systolic ejection of the ventricular volume curve during the Valsalva maneuver markedly diminished. The stroke volume during the Valsalva maneuver for the band at the lower rib cage placement fell to 67% of the baseline, and rose 29% above baseline upon release of the Valsalva maneuver. There was a concomitant rise in the carotid arterial pressure pulse recorded with NIP, but the waveform of BP failed to disclose this rise. The findings in FIG. 10 are similar to those obtained with left ventricular angiography in which the fall in stroke volume derived from ventricular volume measurements fell from 35 to 75% of the baseline during the straining period. Similar declines of stroke volume (53%) have also been obtained using an intracardiac impedance catheter in the right ventricle. Echocardiography measurements of ventricular volumes in both healthy subjects and patients with congestive heart failure demonstrate similar reductions in stroke volume during Valsalva maneuvers.

Figure 11:
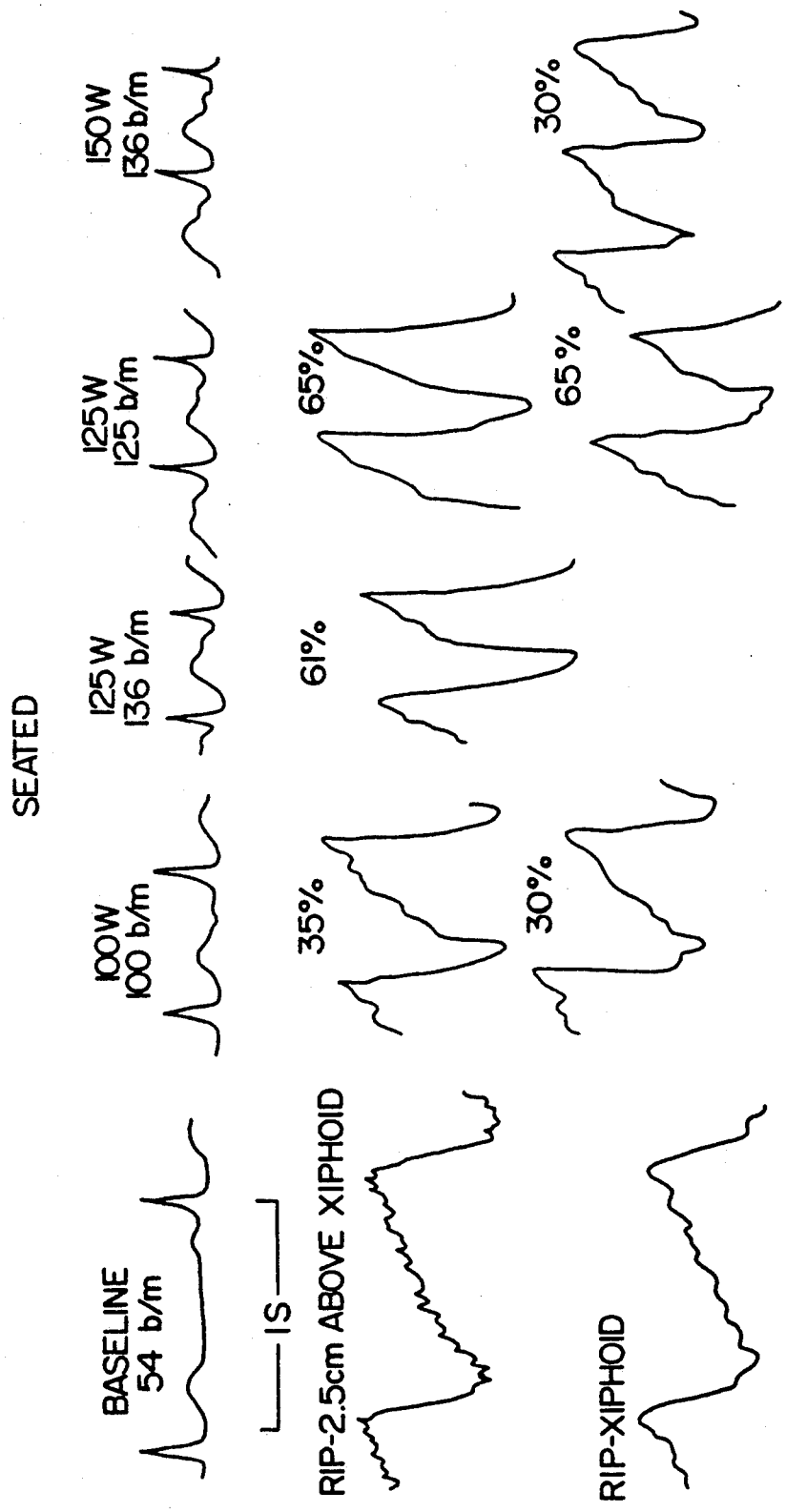
FIG. 11 depicts waveforms showing the effect of exercise on stroke volumes.
Figure 12:
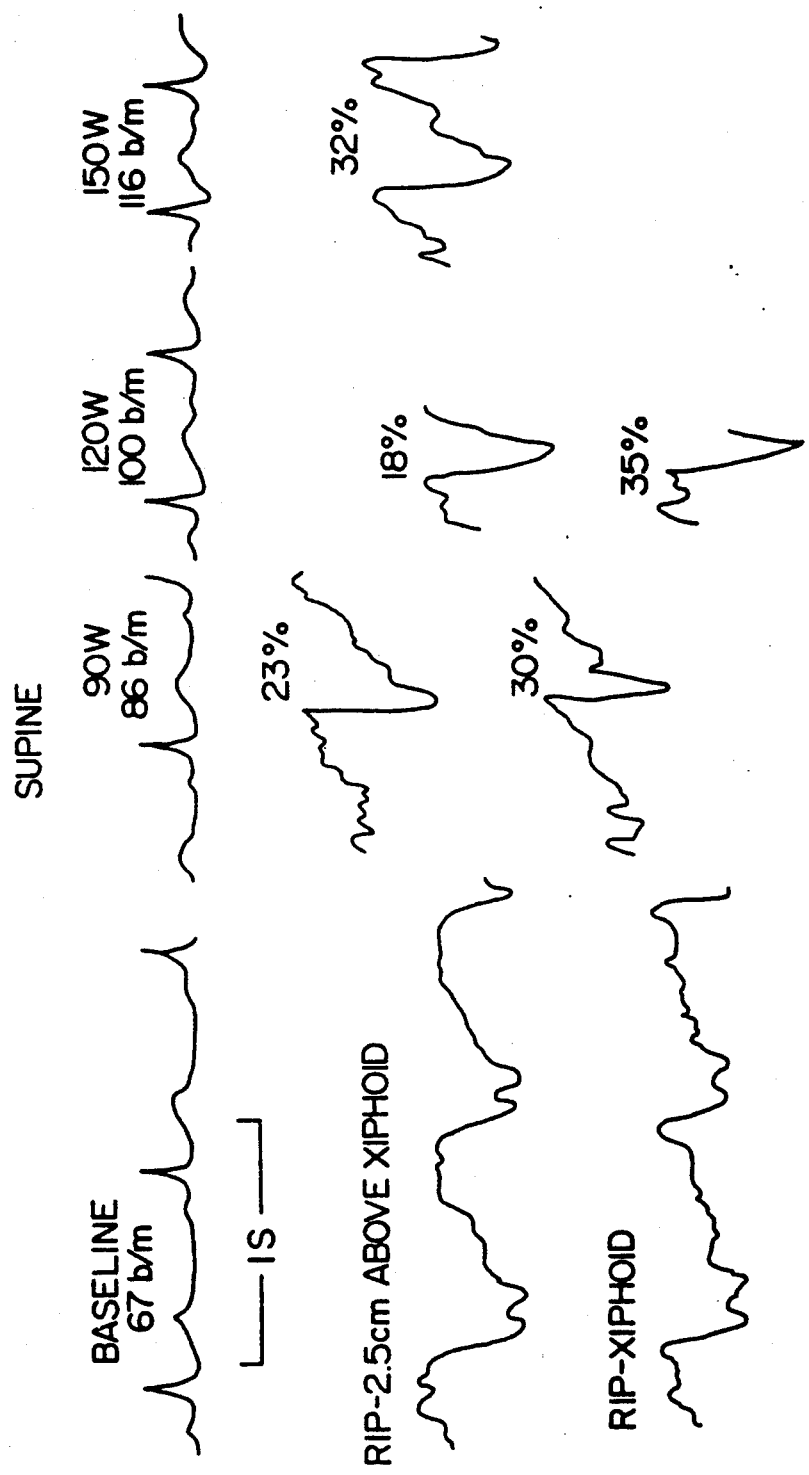
FIG. 12 depicts waveforms showing the effect of exercise on stroke volume with the subject in the supine posture.

The effect of exercise upon stroke volume depends upon the body posture in which exercise is carried out. In normal adults, utilization of dye dilution techniques for cardiac output allows calculation of stroke volume by dividing cardiac output by heart rate. During walking on a treadmill, one prior art study showed that stroke volume had an initial large rise with light exercise, i.e. heart rate rose from a baseline of 87 b/m to 115 b/m and stroke volume increased 69%. Stroke volume continued to rise slightly with more strenuous exercise up to a maximum of 84% above baseline at a heart rate of 171 b/m. On the other hand, in supine bicycle exercise, stroke volume increased only 6% during mild exercise, from a baseline heart rate of 71 b/m to 119 b/m. With moderate exercise, heart rate rose to 127 b/m but stroke volume increased only 13% over baseline. Referring to FIG. 11, in a normal adult instrumented with narrow bands connected to a respiratory inductive plethysmograph and seated on a bicycle, during breathholding immediately after terminating an exercise load, stroke volume increased from 35 to 65% over baseline on the band placed 2.5 cm above the xiphoid, while heart rate increased from 54 b/m up to 125 b/m. Referring to FIG. 12, in the supine posture, the rise of stroke volume with exercise measured with the band was much less than the seated posture, amounting to 32% over baseline, while heart rate increased from 67 b/m up to 116 b/m. The increases of stroke volume exceed those reported for supine bicycle exercise using the dye dilution method for cardiac output but are in agreement for the difference in response of stroke volume to exercise in the seated and supine positions. As shown, the rate of both systolic ejection and diastolic filling of the ventricle as measured with the bands markedly increased with exercise.

Figure 13:
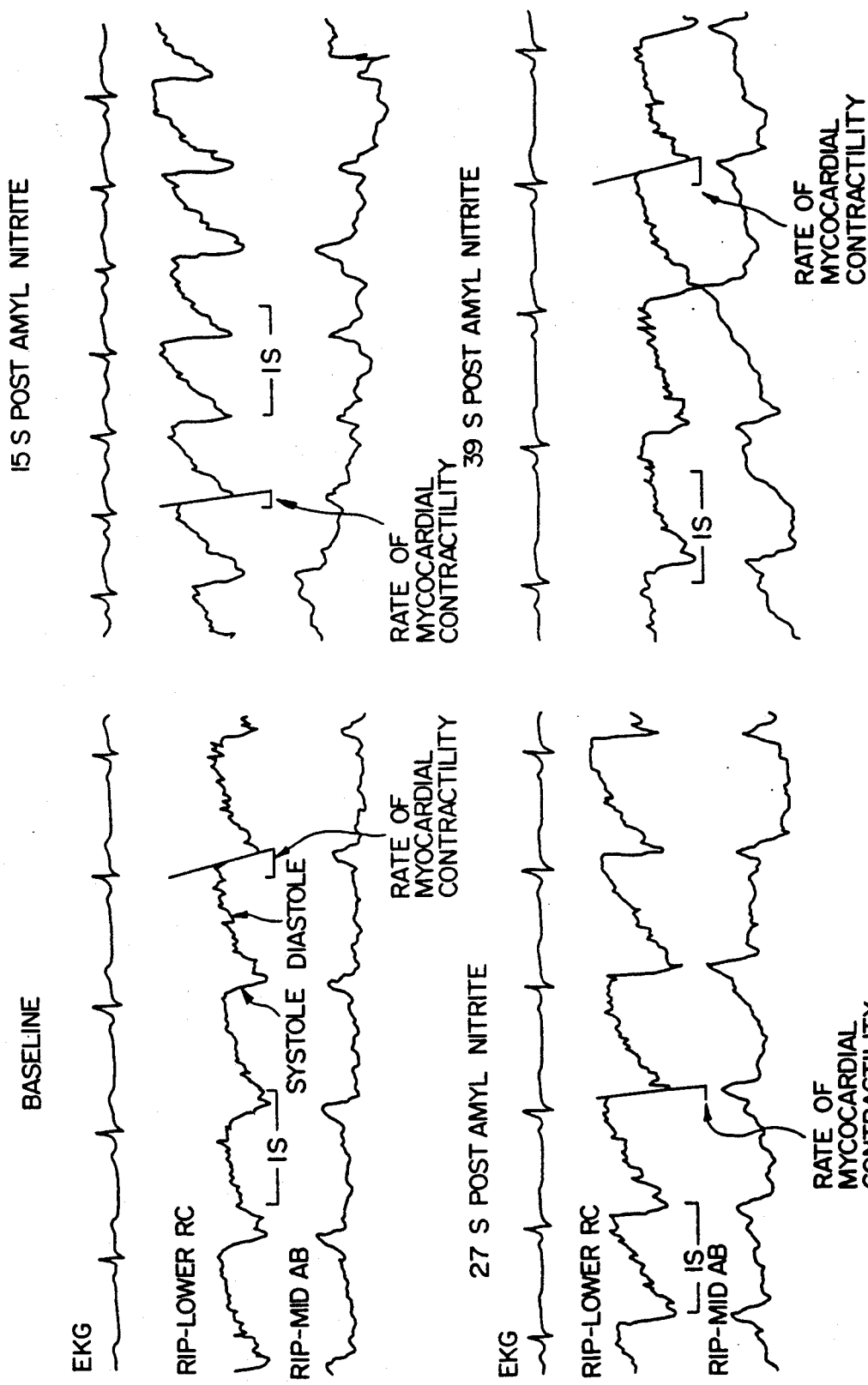
FIG. 13 shows the effect of amyl nitrite on ventricular volume curves derived in accordance with the present invention.

Amyl nitrite, a vaporized compound at room temperature which is administered by nasal inhalation, produces an immediate fall in systemic vascular resistance associated with secondary alterations of cardiac hemodynamics. FIG. 13 shows the effect of this drug on the ventricular volume curve in a supine normal adult as reflected by measurements taken with a respiratory inductive plethysmograph with a wide band place at the lower rib cage placement and on the abdominal aortic pressure pulse as reflected by measurements taken with a wide band at the mid-abdominal placement. Fifteen seconds after inhalation of amyl nitrite, stroke volume increased 39% above baseline and heart rate rose from the baseline of 54 b/m to 84 b/m. Myocardial contractility markedly increased as indicated by the more rapid slope of systolic ejection after amyl nitrite. There was also a more rapid rise in filling during the diastolic portion of the ventricular volume curve. The increased rate of myocardial contractility was also present 27 seconds after amyl nitrite administration when the heart rate had slowed to 67 b/m. Thirty seconds after amyl nitrite administration, the heart rate was slower than baseline at 48 b/m and myocardial contractility returned to baseline value. Thus, measurement of ventricular volume curves with the respiratory inductive plethysmography in accordance with the invention provides a beat by beat recording during breathholding of the alterations expected from a drug which increases myocardial contractility and cardiac output. Of course, this information could also be derived during breathing by employing ensemble averaging or the curve fitting technique as more fully described above.

Figure 14:
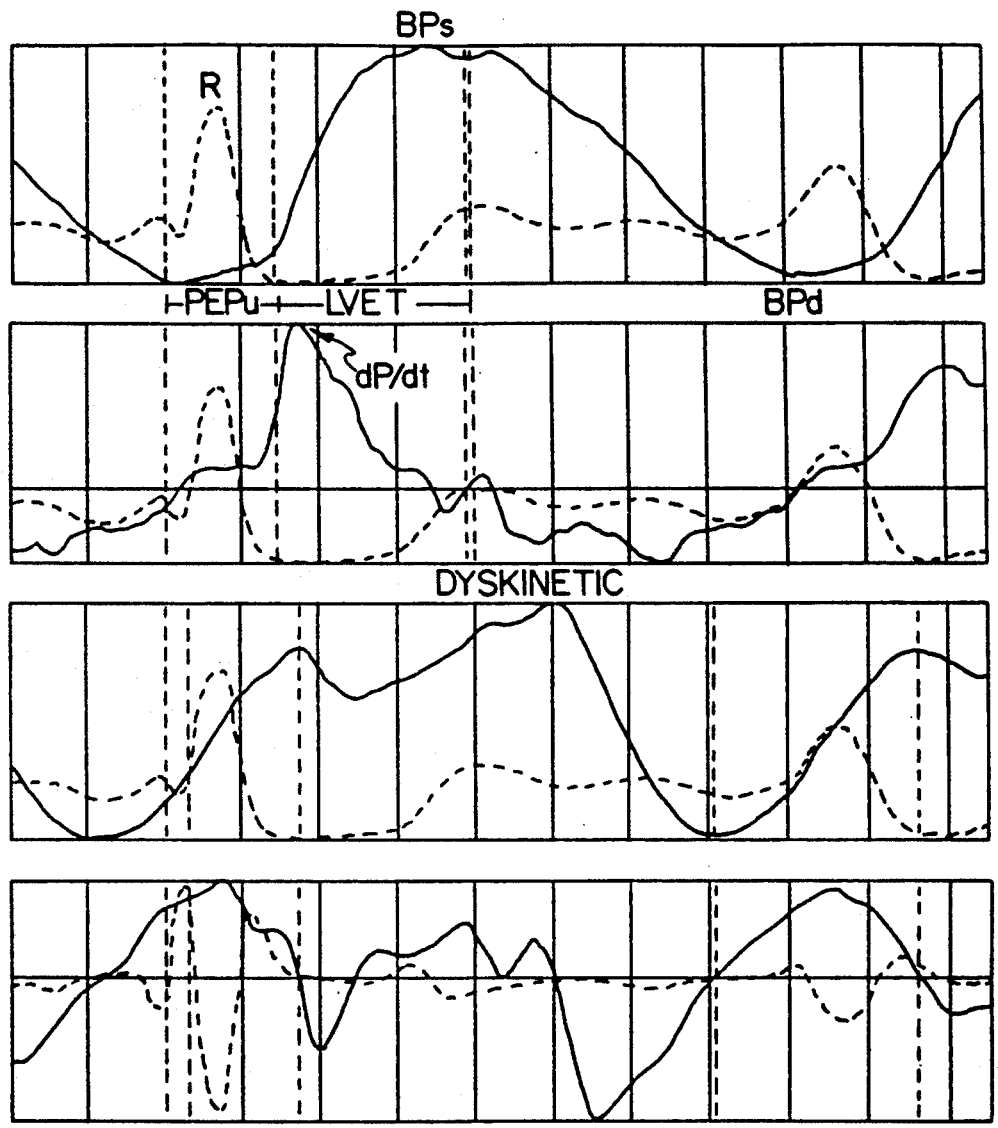
FIG. 14 is a recording of a carotid arterials waveform and a left ventricular volume curve in a subject with ischemic heart disease.
Figure 15:
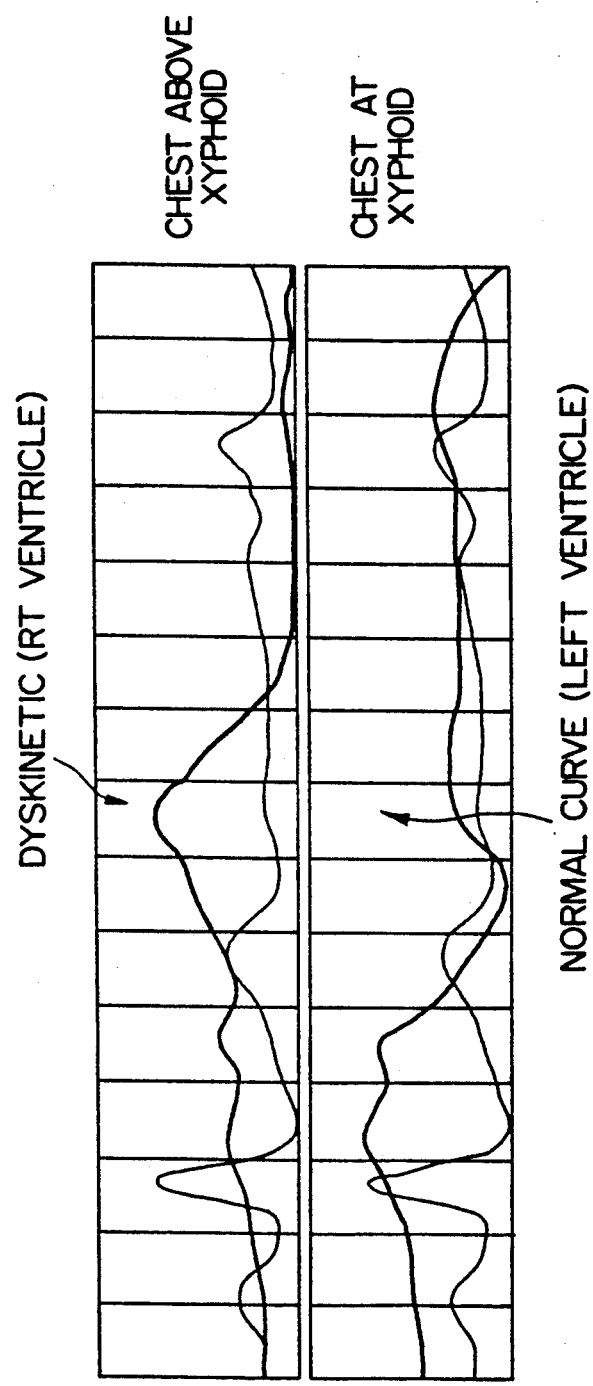
FIG. 15 is a waveform derived in accordance with the present invention and showing dyskinetic motion of a ventricle segment resulting from pulmonary hypertension.

Acute myocardial infarction with/without subsequent healing may produce paradoxical, dyskinetic or akinetic motion of the injured segment of the ventricle. In addition, silent ischemia may also induce such changes. FIG. 14 depicts a dyskinetic ventricular volume curve in a patient with ischemic heart disease. More particularly, FIG. 14 shows a recording of a carotid arterial waveform and left ventricular volume curve in a patient with ischemic heart disease BPs systolic blood pressure; BPd diastolic blood pressure; PEPu=pre-ejection period uncorrected for pulse waveform delay; LVET=left ventricular ejection time; dP/dt=maximum rate of rise of carotid arterial waveform. Ventricular wall dyskinesis is shown in the third recording from the top. Note that the time from the R wave of the EKG to Peak Ejection Rate (PER) is markedly prolonged to 520 ms. Identical findings were obtained with echocardiography. Dyskinetic motion also may be present in patients with pulmonary hypertension in whom right ventricular enlargement is present. This event has been detected with bands located 5 cm above the reference band (placed just below the xiphoid process) which showed a normal left ventricular volume curve contour (FIG. 15).

Figure 16:
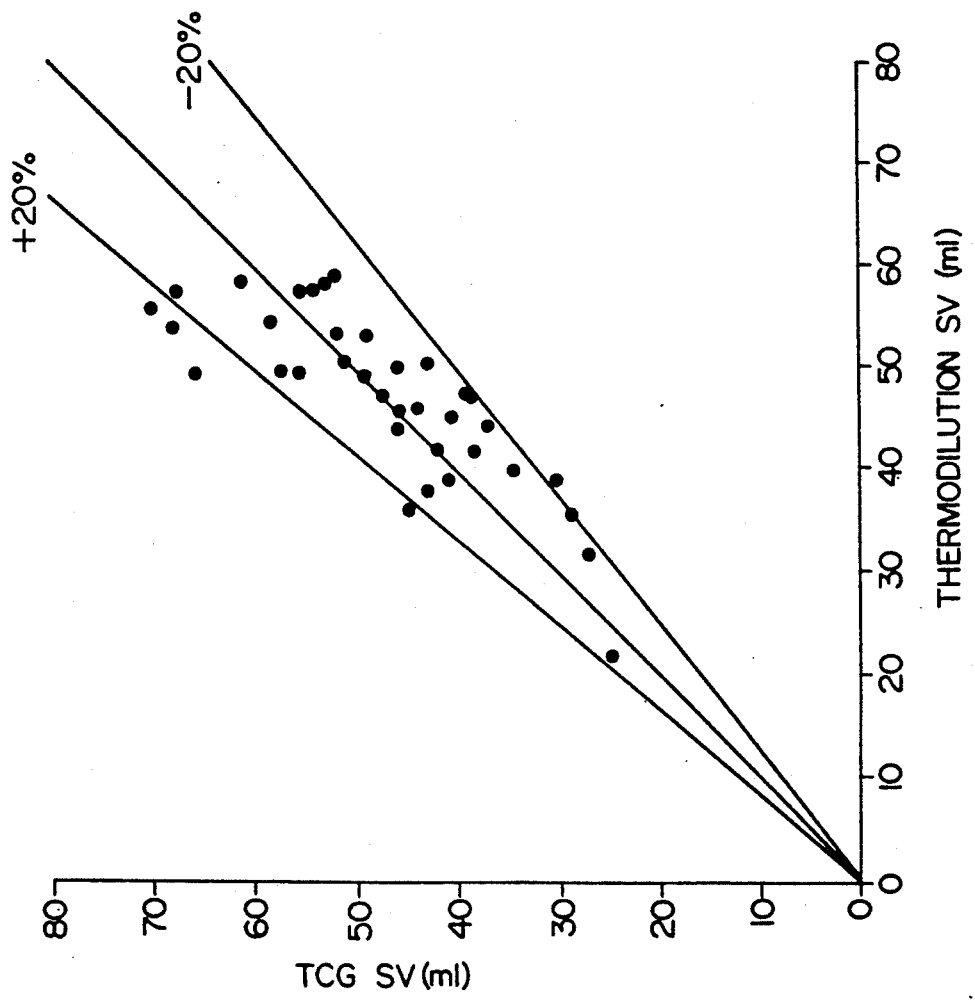
FIG. 16 is a graphic representation of a comparison of stroke volume measurements derived in accordance with the present invention and in accordance with the thermodilution method.

Cardiac output can be measured by the thermal dilution method using a Swan-Ganz cardiac catheter whose tip is placed within the pulmonary artery. Stroke volume is calculated by dividing the cardiac output by heart rate. This value can be used to calibrate the systolic portion of the ventricular volume curve (obtained with a narrow band sensor or similar transducer) to an absolute volume value in the baseline period. Thereafter, this value can be utilized for all subsequent calculations of stroke volume from the ventricular volume curves to ascertain both the absolute volume variations and to establish the validity of the non-invasive measurement. The accuracy of the latter depends upon the assumption that the ventricle can be considered as moving with one degree of freedom but this assumption can only be proven by comparing the thermodilution method (or other cardiac output method) to the measurements made with the non-invasive TCG technique. This experiment was carried out in six anesthetized dogs. Baseline values were obtained by simultaneous collection of narrow band derived (TCG) and thermodilution values of stroke volume and cardiac output. The animals were then give 50 ml infusions of a 10% dextran 40 solution every 15 minutes with repeated simultaneous measurements at each time interval until cardiac output by the thermodilution method no longer increased with further dextran 40 infusions. Stroke volume by the thermodilution method rose to a maximum of 40% above the baseline value. In 46 paired comparisons, 87% of stroke volume values based on the TCG fell within 20% of stroke volume measurements based on thermodilution values (FIG. 16). Therefore, TCG appears to provide an accurate measure of changes of stroke volume and cardiac output in anesthetized dogs.

Figure 17:
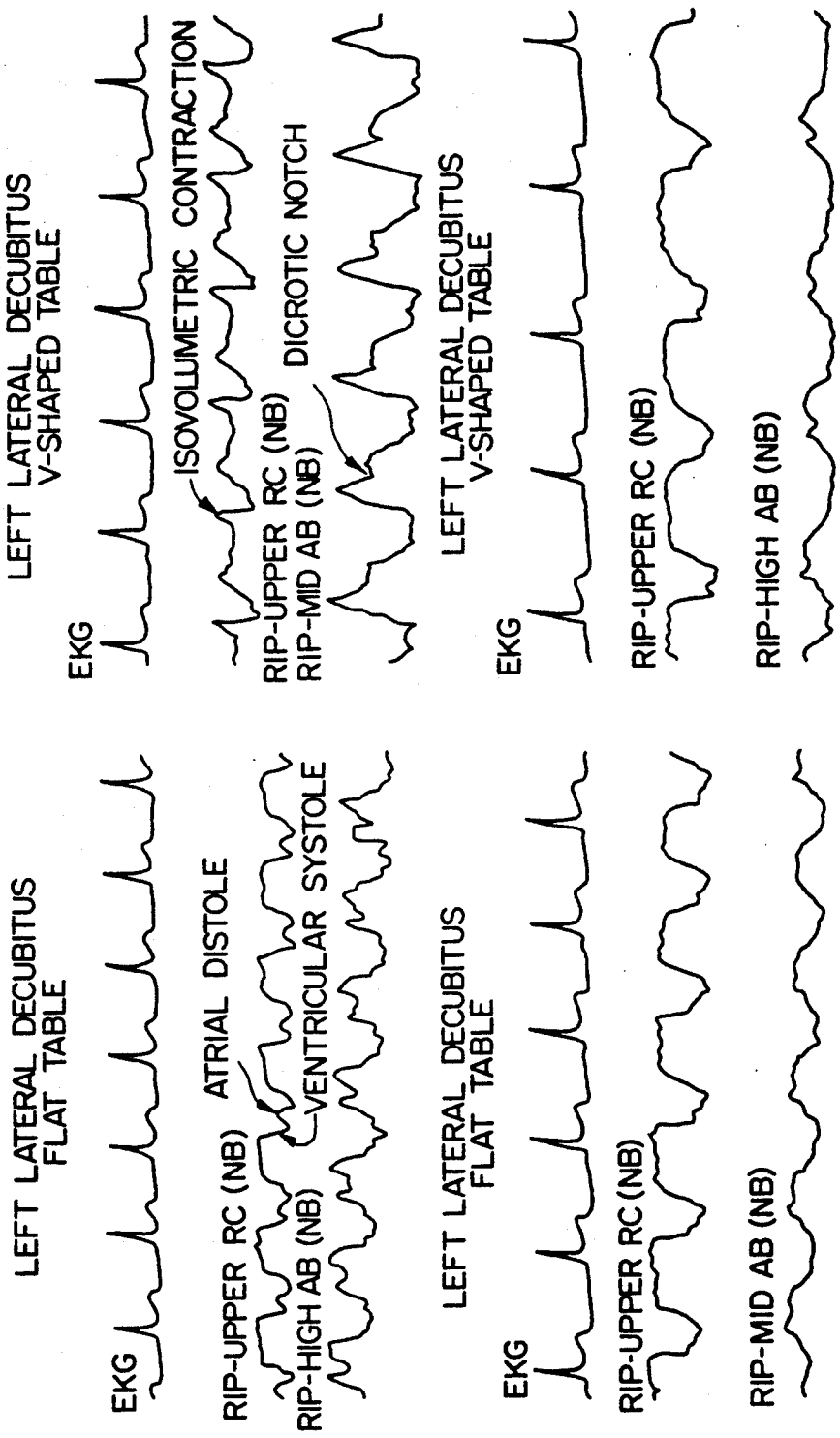
FIG. 17 depicts waveforms derived using narrow band sensors in accordance with the present invention and showing ventricular volume curves derived from dogs with various band placements and body postures.

Because the rib cage of the dog is highly compliant much like the rib cage of a human baby, a study was undertaken to determine if it would be possible to obtain satisfactory recordings of ventricular volume curves using bands on the rib cage and abdomen in dogs. FIG. 17 depicts recordings of bands placed around the upper rib cage of the dog just underneath the axilla with variations of placement approximately 1 to 2 cm upward or downward. The left panels depict recordings when the dog was in the left lateral decubitus position on a flat table. The upper left panel shows a typical ventricular volume curve along with a superimposed rounded upward wave of atrial diastole at the nadir of ventricular systole. In the lower left panel, the band has been moved downward about 1 cm and the wave of atrial diastole is now eliminated. There is absence of the isovolumetric contraction phase of the ventricular volume curve in the upper left panel as indicated by the tracing labeled "RIP-upper RC (NB)", which connotes a narrow band placed at the upper rib cage and connected to a respiratory inductive plethysmograph, but a prominent upward deflection on the right upper panel. The bands on the mid-upper abdomen were considerably dependent upon their placement site. When the dog was placed on a V shape table to support the body in a different orientation, the mid-abdominal band on the upper right panel showed a typical waveform of the abdominal aortic pressure pulse with an easily recognizable dicrotic notch. Other band placements also gave abdominal aortic pressure pulses.

It is clear from the foregoing description that external monitoring with non-invasive sensors which measure rib cage and abdominal movements are capable of recording cardiovascular events in adults, babies and animals. With appropriate sensors and data processing, recording of segmental ventricular volume curves and aortic pressure pulses on a beat by beat basis during breathholding is possible. Average waveforms can be obtained during breathing through the technique of ensemble-averaging, using as a trigger the QRS complex of the electrocardiogram or the upstroke of a systemic arterial pulse recorded either non-invasively or invasively. Alternatively, the curve fitting techniques and adaptive digital filtering techniques may be employed to extract the cardiogenic waveforms from the respiratory waveform. Further, waveforms of ventricular volumes and aortic pulses at different cardiac cycle length, and at various points in the lung volume level and airflow, can also be obtained. The technology described herein carries major implications in terms of physiologic, pharmacologic and clinical understanding of cardiac function and diagnosis of heart disease in adults, babies, and animals.

Figure 18:
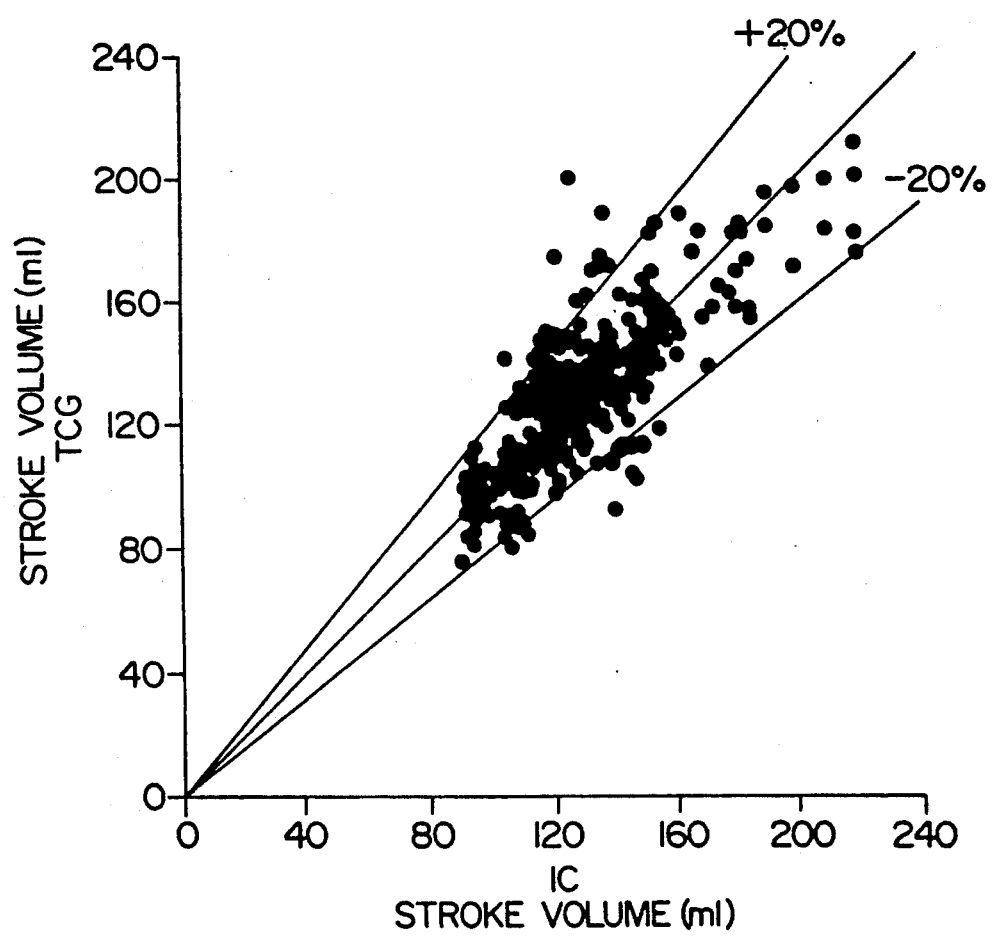
FIG. 18 is a graphic representation comparing stroke volume as determined in accordance with the present invention and as derived using impedance cardiography.
Figure 19:
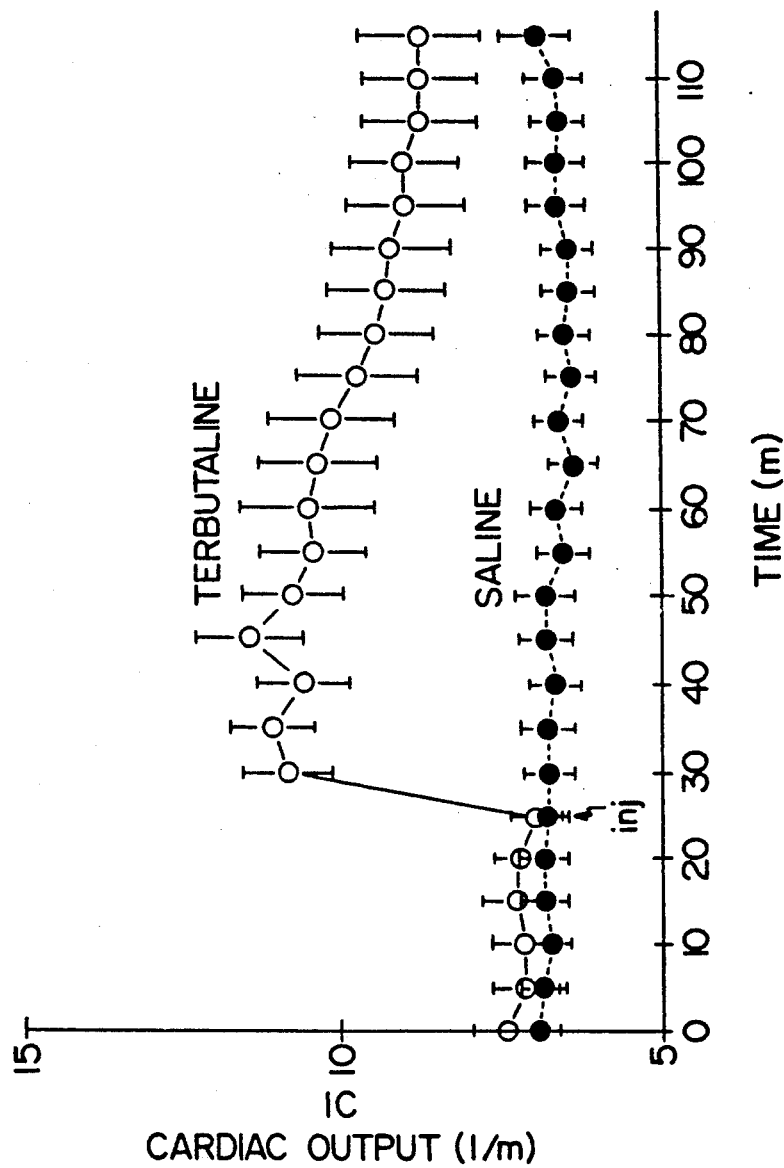
FIG. 19 is a graphic representation of cardiac output as derived from impedance cardiography upon injection with terbutaline and saline.
Figure 20:
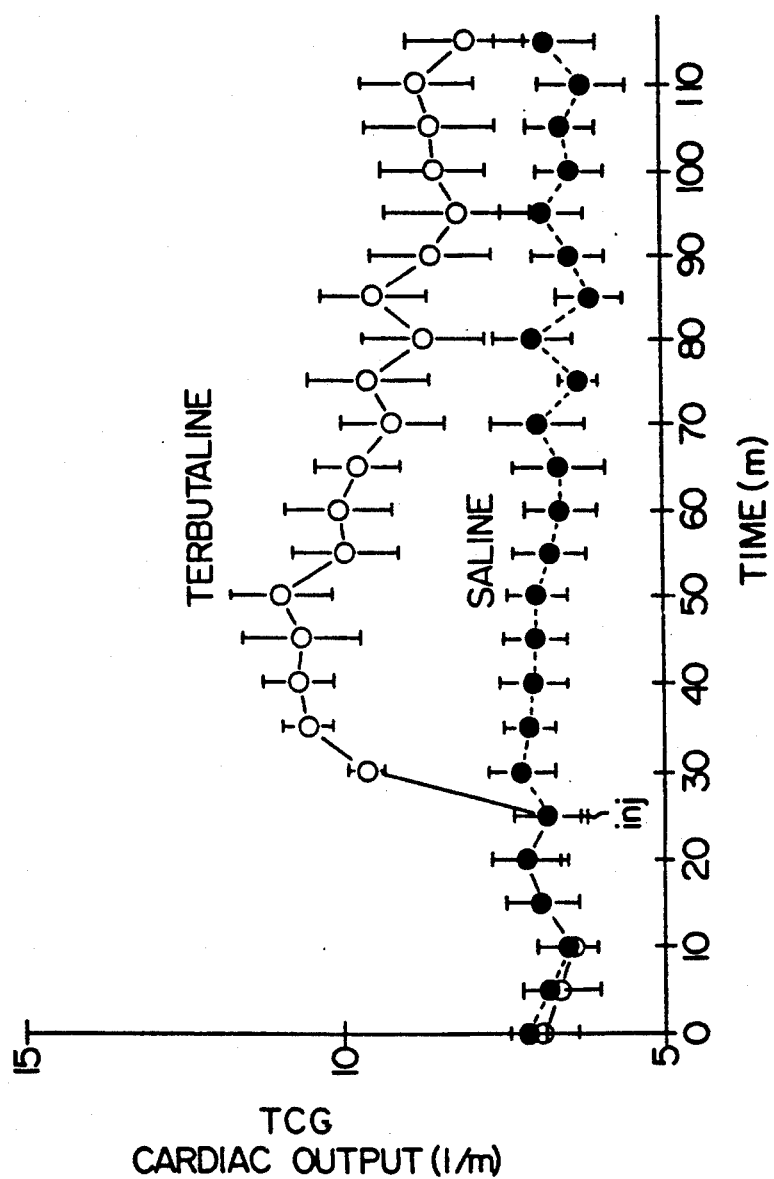
FIG. 20 is a graphic representation for comparison with FIG. 19 and showing cardiac output as derived in accordance with the present invention upon injection of terbutaline and saline.

It is impractical to measure stroke volumes and cardiac output with the invasive thermodilution technique in normal human subjects in order to establish the validity of the thoracocardiogram (TCG) for measuring changes of stroke volume (SV) and cardiac output (CO). There is ample evidence in the literature that the impedance cardiograph can measure changes of stroke volume and cardiac output if body posture is fixed. This device uses an empirical equation and an assumption that the thorax can be treated as a single conductor to derive values of stroke volume. The waveform from this devices resembles an aortic pulse and is opposite in polarity to the ventricular volume waveform obtained with the thoracocardiograph. Values of stroke volume measured by the thoracocardiogram [SV(TCG)]were compared to SV measured by impedance cardiograph (IC) in six normal semirecumbent men after subcutaneous injection of 0.25 mg terbutaline to cause increased SV. On another day, 1 ml of saline was injected subcutaneously to serve as a control. Data from TCG and IC were collected every five minutes during a 30 minute baseline and 90 minutes after injection. Maximum increases of SV and CO after terbutaline were 27% and 50%, respectively; SV and CO were not altered by the saline injection. In 288 paired comparisons, 91% of SV(TCG) values fell within 20% of SV(IC) (FIG. 18). Further, there was no statistically significant differences between IC and TCG derived cardiac outputs at any time point in the preceding investigation (compare FIGS. 19 and 20). These data indicate that TCG derived ventricular volume curves accurately estimate changes of stroke volume and cardiac output.

The configuration of the ventricular volume curve provides indices of systolic and diastolic function of the heart. For systolic function, these intervals and volume ratios were compared to systolic time intervals which are well known timing measures of the carotid arterial pulse, to establish relationships for systolic function between these two different measurements of cardiac contractility. In the first series of experiments, effects of terbutaline were investigated.

Terbutaline has been purported to be a beta-2 adrenergic agonist but its administration is associated with a marked, sustained increase of cardiac output (CO). The latter is attributed to systemic vasodilation and possibly enhanced ventricular contractility. See Chest, volume 68, pages 616 et seq., 1975. To further characterize its action, several non-invasive cardiovascular monitoring techniques were employed. The left ventricular volume curve (LVVC) was displayed as an averaged cardiogenic oscillation with the thoracocardiograph (TCG). The respiratory signal was eliminated by an ensemble-averaging method. In addition to systolic and diastolic volumes from LVVC (TCG), other parameters were measured: (1) heart rate (HR) by EKG; (2) blood pressure (BP) by cuff auscultation; (3) systolic time intervals from the carotid pulse obtained by comingation of an inductive plethysmograph band around neck and the EKG (4) dP/dt of carotid pulse after calibration with BP; and (5) ejection fraction (EF) by equation utilizing PEP/LVET (PEP=pre-ejection period and LVET=-left ventricular ejection time). In a 2 day crossover study, 5 normals received terbutaline 0.25 mg subcutaneously or saline and data were analyzed at baseline and peak response, 10–20 minutes after injection. Compared to saline, terbutaline produced significant rises over baseline in HR (20%), LVETI (8%) [LVETI left ventricular ejection time index], EF (16%), stroke volume (28%), cardiac output (54%), peak ejection rate (PER) (61%), dP/dt (70%) and left ventricular stroke work (27%). Terbutaline significantly decreased diastolic BP (9%), PEPI (20%), PEP/LVET (31%) R to PER time (13%) [R=R wave and PER=peak ejection wave] and peripheral vascular resistance (43%). Early diastolic filling flows, volumes and timing were not altered. The simplest and most consistent parameter of the systolic portion of the LVVC was shortening of R-PER time, easily recognized points on the EKG and TCG waveforms, respectively.

The systolic amplitude of the ventricular volume curve can be utilized to estimate trends in stroke volume, and in conjunction with an invasive technique such as thermal dilution or dye dilution, or a non-invasive technique such as impedance cardiography or echocardiography, etc., the ventricular volume waveform can be calibrated to an absolute volume. Measurements can be obtained with the standard (wide) or narrow band transducers of the respiratory inductive plethysmograph, but alternatively other non-invasive sensing devices that have been utilized for measuring breathing movements can also capture cardiovascular events as a function of the height subtended by their transducers. The respiratory inductive plethysmograph is preferable to other such devices because it can provide accurate display of ventricular volume curves independent of postural changes in the horizontal plane, whereas other respiratory monitoring devices generally cannot accurately record ventricular volume curves in the prone or lateral decubitus postures. The product of heart rate times stroke volume equals cardiac output. With the invention, cardiac output measurements can be obtained at rest and exercise in both normal and diseased subjects. These measurements can be recorded during breathholding on a beat by beat basis or during breathing with display of the average ventricular volume curve by ensemble-averaging using the QRS wave of the electrocardiogram or upstroke of a systemic arterial pulse as a trigger, or by using curve fitting or adaptive digital filtering techniques as described above to extract the cardiogenic waveform from the respiratory waveform. Further, ventricular volume curves can be recorded in sleeping humans or animals during spontaneous central apneas, obstructive apneas or during breathing. This should permit analsis of the effect of such entities as Obstructive Sleep Apnea Syndrome on cardiac performance and guide therapeutic interventions.

The electronics of any of the sensors mentioned above can be miniaturized such that they can be incorporated into a tape recorder, compact disc, etc.—Holter monitoring device to carry out ambulatory monitoring for both electrical activation of the heart through the electrocardiogram and its mechanical response as detected by the present invention for non-invasively recording ventricular volume waveforms and aortic pressure pulse. This should be useful in characterizing cardiac arrhythmias and the effects of cardiac ischemia on cardiac performance.

Figure 21:
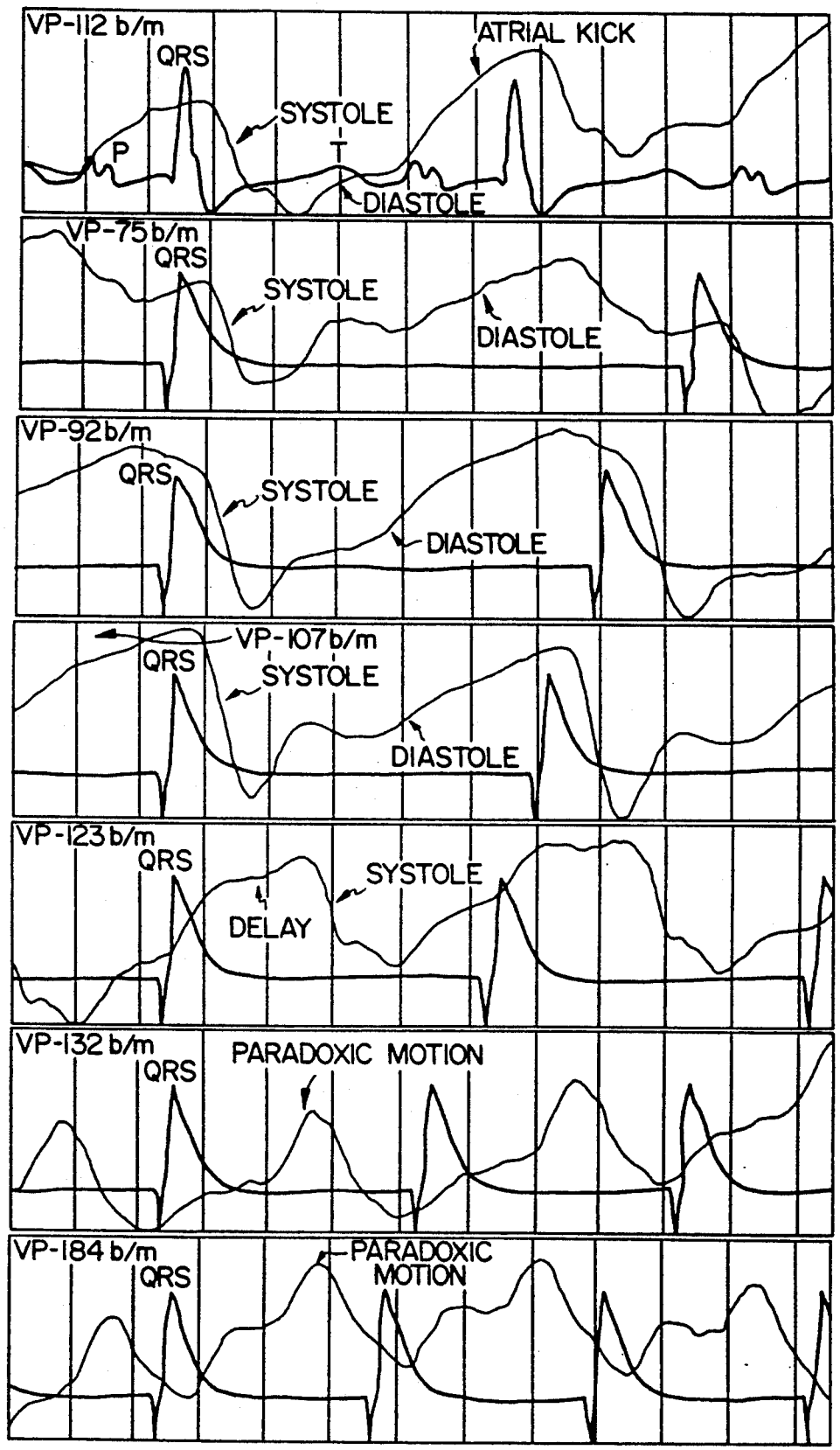
FIG. 21 is a series of recordings showing the effect of externally pacing the right ventricle on the ventricular volume curve of a mechanically ventilated, anesthetized dog.

FIG. 21 illustrates the effects of externally pacing the right ventricle on the ventricular volume curve of a mechanically ventilated, anesthetized dog. The data were obtained by ensemble-averaging using the QRS wave of the EKG as the trigger signal. The uppermost tracing depicts the unpaced ("UP") EKG and ventricular volume curve; here the heart rate was 112 beats/minute. At ventricular pacing ("VP") heart rates below the unpaced heart rate (75 b/m, 92b/m and 107 b/m), the ventricular volume waveform has a similar appearance and timing relation to the QRS as the unpaced recording. However, at higher ventricular pacing rates (123 b/m, 132 b/m and 184 b/m), there is a marked delay relative to the QRS due to paradoxic (dyskenesis) of the ventricular segment subtended by the inductive plethysmographic transducer. The ventricular volume curves of FIG. 21 were obtained with a band sensor placed at the xiphoid process of the dog.

The recording of both the electrocardiogram and the ventricular volume waveform might help to differentiate supraventricular tachycardia with aberrant electrical conduction from ventricular tachycardia in which the QRS complex is indistinguishable. These two arrhythmias require different modes of management, as the ventricular tachycardia is an immediate life-threatening cardiac arrhythmia whereas supraventricular tachycardia with aberrant conduction is not. The differentiation may be possible by three means: 1) recording of atrial diastole from a band placed 10 to 15 cm above xiphoid (FIGS. 2 and 3) in a manner analogous to jugular venous pulsations for recording of regular atrial contractions during supraventricular tachycardia, 2) observing abnormal ventricular waveforms with timing and phase abnormalities along with dyskinetic wall motion as in ventricular pacing, or 3) loss of the isovolumetric contraction period of the ventricular volume curve.

Although continuous electrocardiographic recording over 8 to 24 hours with a tape recorder (Holter monitoring) is often utilized to detect transient cardiac ischemia (impaired blood supply to the ventricular muscle) as reflected by alterations of the ST segment and T wave of the electrocardiogram, it is well recognized that the usefulness of this approach is limited by artifacts and the major applicability of Holter monitoring resides in diagnosis of cardiac arrhythmias. However, segmental abnormalities of ventricular wall motion may precede electrocardiographic abnormalities. Thus, the combination of electrocardiographic Holter recording and segmental ventricular volume waveforms with bands or other devices for sensing rib cage movements should improve the diagnostic accuracy of detecting myocardial ischemia both in patients who have chest pain and those who do not (silent ischemia).

Measurement of changes of cardiac output in patients who are critically ill should help to guide therapeutic decisions, either through the use of appropriate doses of drugs and fluids, or with surgical interventions. The utilization of ventricular volume waveforms to estimate stroke volume in critically ill patients provides information regarding the effects of intravenous fluid challenge, i.e., if intravenous fluids are given and cardiac output increases, then the therapeutic intervention probably is appropriate. On the other hand, if intravenous fluid is administered and cardiac output remains the same or falls, then the fluid challenge is probably inappropriate. This algorithm might diminish the utilization of invasive Swan Ganz catheters placed in the pulmonary artery which are also used to ascertain whether fluid challenges are appropriate through cardiac output measurement and pulmonary arterial and left atrial (wedge) pressure recordings. The employment of such technology carries major risks to the patient, including death, and to the health care worker the risk of viral hepatitis and AIDS because of exposure to blood products. Noninvasive monitoring in accordance with the present invention poses no hazards to the patient nor health care workers while still providing similar hemodynamic information. The ventricular volume waveforms along with the electrocardiogram can be obtained at the bedside or transmitted to a video-based central station computerized display for data processing either through hard wire connections or telemetry.

Although cardiac output is an important parameter in guiding management of patients, trending of systemic oxygen delivery ($DO_2$) may be a more valuable test. $DO_2$ is defined as the product of cardiac output and arterial oxygen content. It signifies the volume of oxygenated blood delivered to the tissues. A fall in $DO_2$ produced either by decreased cardiac output, decreased arterial oxygen content or both can cause tissue ischemia and tissue death. Since arterial oxygen capacity is a function of the amount of hemoglobin in the blood, viz. 1.34 ml of oxygen can combine with 1 gm of hemoglobin, one can calculate oxygen content by multiplying the oxygen capacity of the blood by arterial oxygen saturation. The latter can be obtained non-invasively by means of a commercially available device, the pulse oximeter. If hemoglobin content of the blood is stable, then relative changes in $DO_2$ can be obtained by multiplying arterial oxygen saturation by cardiac output. Thus, trends of $DO_2$ can be monitored non-invasively using pulse oximetry and TCG.

To illustrate the importance of $DO_2$ measurements, consider the effects of breathing a hypoxic mixture. It has been reported that breathing a hypoxic mixture ($F_IO_2=0.1$) for 7 to 20 minutes increases heart rate (HR) 24%, stroke volume (SV) 16% and cardiac output (CO) 38% compared to room air (6 publications, 64 normals); CO was measured by indicator dilution techniques. I extended such observations by administering graded hypoxic mixtures for 12 minutes, viz. $F_IO_2$ of 0.17, 0.15, 0.12 and 0.10 to 7 normals to establish dose-responsiveness for cardiac performance and oxygen delivery ($DO_2 = CaO_2 \times CO$). SV and CO were measured with the thoracocardiograph (TCG). In addition, oxygen saturation ($SaO_2$) from pulse oximetry, ejection fraction (EF) from an equation involving PEP/LVET, and minute ventilation ($V_I$) from RIP were obtained. The table below lists mean $SaO_2$ and fractional changes of other parameters compared to $F_IO_2=0.21$ ($SaO_2=96\%$). In the table, an "*" denotes a statistically significant difference from $F_IO_2=0.21$.

| $F_IO_2$ | $SaO_2$ | HR    | SV    | CO    | EF    | R-PER | $V_I$ | $DO_2$ |
|----------|---------|-------|-------|-------|-------|-------|-------|--------|
| .17      | 90*     | 1.03  | 1.01  | 1.03  | 1.02  | .97*  | 1.06  | .98    |
| .15      | 88*     | 1.05* | 1.04  | 1.07  | 1.05* | .96*  | 1.16  | .99    |
| .12      | 76*     | 1.19* | 1.10* | 1.30* | 1.08* | .90*  | 1.22* | 1.03   |
| .10      | 67*     | 1.27* | 1.19* | 1.48* | 1.08* | .87*  | 1.20* | 1.03   |

In the table, $F_IO_2$ = fractional concentration of oxygen in gas mixture (room air = 0.21); $SaO_2$ = arterial oxygen saturation; HR = heart rate; SV = stroke volume; CO = cardiac output; EF = ejection fraction; R-PER = interval from R wave of EKG to peak ejection rate on TCG ventricular volume curve (FIG. 22); $V_I$ = minute ventilation; and $DO_2$ = systemic oxygen delivery. Changes of HR, SV and CO at $F_IO_2=0.1$ agree well with prior reported values. In normals, CO rose proportionally so that $DO_2$ was maintained constant with brief graded decrements of $SaO_2$. This illustrates the importance of considering $DO_2$ rather than CO alone. Not surprisingly, there were no untoward symptoms in these subjects despite falls in $SaO_2$ to values as low as 55%. Estimation of $DO_2$ with decreased $SaO_2$ in normal and diseased states over prolonged time intervals needs investigation since $DO_2$ ultimately determines tissue viability.

In contrast to grade hypoxia and terbutaline administration experiments, head-up tilting of normal subjects produces decreased cardiac output and decreased cardiac contractility. The amplitude of the TCG derived ventricular volume curve may not accurately reflect the fall in stroke volume owing to changes in the volume-motion coefficient of the rib cage with major changes of body posture as in changing from supine to upright postures. However, the configuration of the curve is altered in an expected way and provides useful information on contractility, viz. instead of a shortening of the R-PER interval as in hypoxia and after terbutaline injection, head-up tilting causes the R-PER interval to lengthen, a finding consistent with decreased cardiac contractility.

The monitoring of trends in cardiac output during anesthesia using the non-invasive sensor placed upon the surface of the rib cage in patients undergoing peripheral or abdominal (i.e. non-chest related) surgical operations provides a valuable measure of cardiac performance. It is well known that anesthetic agents and surgical interventions often deleteriously affect cardiac output.

Evaluation of appropriate cardiac pacing rates and the effects of different pacing sequences on stroke volume is an important consideration in cardiac pacemaker therapy. This can be accomplished by analysis of beat to beat stroke volume estimations from ventricular volume waveforms obtained with external sensors placed on the rib cage. In addition, control of optimal pacing rates through a servo loop can be accomplished by monitoring stroke volume to reset the pacing rate for optimal stroke volume performance during exercise. This has already been carried out on a research basis with an intracardiac placed catheter for beat to beat changes of cardiac impedance.

The monitoring of ventricular volume curves should also be useful in evaluating changes of cardiac output in subjects confined to inaccessible environments such as the magnetic resonance imaging device, space capsules, diving bells, diving suits, high and low pressure chambers etc.

Measurements of stroke volume during various mechanical ventilatory modalities should help to establish mechanical ventilator settings which least deleteriously affect cardiac output. The ventricular volume waveform measured with external sensors on the rib cage can be obtained during mechanical ventilation by the ensemble-averaging, curve fitting and other adaptive digital filtering techniques as described above to extract the cardiac waveform.

The Valsalva maneuver viz. straining with a closed glottis decreases stroke volume as shown above from measurements of the ventricular waveform in a normal subject. The stroke volume normally increases after the straining maneuver is halted and the glottis is opened. Such a response may not occur in patients with heart disease and therefore the maneuver may help to differentiate normal subjects from patients with heart disease.

In addition to using the respiration signal for monitoring breathing patterns in babies with near SIDS (Sudden Infant Death Syndrome), monitoring of stroke volume and cardiac output from non-invasive determinations of ventricular volume curves as described above should aid in the early detection of cardiac abnormalities since it is known that bradycardia is often associated with apneas in these babies.

Since the invention provides a mechanical indication of cardiac performance, it will be useful in establishing a timely diagnosis of death from cardiac standstill even though electrical activity of the heart may still be present.

The rapidity of ventricular emptying as a measure of myocardial contractility can be obtained as the slope of the ventricular volume waveform from the external sensing device placed on the rib cage during systole or by taking an electrical analog or digital derivative of this waveform. The slope of rapid filling for the ventricular volume curve at the end of isovolumetric relaxation provides a measure of the mechanical characteristics of ventricular muscle. The slope of late diastole provides a measure as to whether the heart is filled, has limited diastolic reserve, or has a great deal of diastolic reserve as indicated by a upward sloping deflection of this portion of the curve. All the situations discussed in the preceding sections, regarding cardiac output and stroke volume, apply for the importance of analyzing the configuration of the ventricular volume waveform to assess cardiac performance.

The configurations of the ventricular volume and aortic pressure pulses may be abnormal in patients with heart disease at rest, exercise, sleep, and with environmental stresses, e.g. temperature, humidity, etc. The waveform of the ventricular volume curve in patients with valvular heart disease has distinctive characteristics. For example, in patients with aortic stenosis the rate of systolic ejection of the ventricular volume curve is diminished whereas in patients with mitral stenosis the rate of diastolic filling is diminished. The upstroke of the aortic pressure pulse is also diminished in aortic stenosis. Patients with coronary artery disease may have limited ventricular wall motion due to ventricular compliance and have slow filling of diastole. Patients with constricted pericarditis or restrictive myocardiopathy may show diastolic plateaus as a result of these defects.

A long flat diastolic plateau has been observed in the ventricular volume curve obtained with the present invention in a patient with pulmonary edema, a pulmonary arterial wedge pressure of 27 mmHg, and an enlarged heart on the chest roentgenogram. This type of waveform presumably indicates ventricular distention and might serve as a non-invasive monitor of left atrial pressure in such patients.

Abnormal ventricular motion takes place with stunned myocardium after myocardial ischemia secondary to occlusion of a coronary vessel or with therapeutic angioplasty in which brief occlusion of the coronary artery supplying a region of ventricular muscle produces abnormal wall motion of this part. Indeed, abnormal wall function during myocardial ischemia precedes electrocardiographic abnormalities and is a more sensitive diagnostic sign. Acute myocardial infarction produces abnormal ventricular volume waveforms which may be reversed by administration of thrombolytic agents. This phenomenon is best studied with segmental sensors over a large height of the rib cage rather than a wide band sensor enclosing the entire ventricle since small regions of abnormal motion might be missed under these circumstances. The configuration of the ventricular volume curve during the Valsalva maneuver in which systolic ejection and stroke volume are markedly diminished in normal subjects, and is followed by an increase of these parameters after release of straining, may not occur in patients with heart disease and thus offers criteria for distinguishing normals from patients with heart disease. Furthermore, changing the configuration of the ventricular volume curve by tilting the subject from the supine to upright postures and vice-versa produces characteristic alterations in the configuration of the ventricular volume waveform. For example, in the standing posture, the terminal diastolic portion of the ventricular volume curve normally slopes upwards whereas in the supine posture terminal diastole has a flat plateau. This signifies that the heart is well filled in the supine but not the upright posture, which might not occur in patients with heart disease.

With narrow band external sensors, ventricular volume waveforms at different portions of the ventricle can be recorded such that timing and motion analysis between the segments can be carried out. This should prove useful in assessing the effects of acute ischemia and myocardial infarction on configuration of the ventricular volume waveform since it is well known that ventricular wall motion is impaired in these circumstances. This can result in dyskinetic, akinetic or hypokinetic motion of segmental portions of the ventricular wall with consequent abnormalities of the segmental ventricular volume waveforms. Using the non-invasive method of the invention with sensors on the rib cage to display segmental ventricular volume waveforms should make possible the diagnosis of such abnormalities and to ascertain the effectiveness of treatment either with intravenous administration of thrombolytic agents or angioplasty of the appropriate coronary artery. Furthermore, long term periodic follow-up with the non-invasive technology of the invention should help in establishing the efficacy of treatment. For example, the effect of coronary artery bypass grafts on segmental ventricular volume curves can be determined post operatively; if follow-up evaluations show new segments of abnormal wall motion different from the baseline established after surgery, then diagnosis of restenosis of the coronary artery might be suspected.

Analysis of segmental ventricular volume configuration with such interventions as cardiac pacing, exercise, Valsalva maneuver, tilt, and drug administration, etc. should enhance its diagnostic effectiveness. The effects of anesthesia agents on ventricular volume waveforms should help to guide decisions on cardiovascular status during surgery. Finally, ambulatory Holter monitoring using the electrocardiograph and segmental ventricular waveform analysis with separation of curves into histograms of cardiac lengths and electrical abnormalities such as the ST-T wave depressions or inversions can be utilized to correlate electrical and mechanical events during arrhythmias and periods of potential myocardial ischemia.

In conjunction with invasive catheterization of the left ventricle, ventricular pressure-volume curves can be constructed to attain a definitive understanding of ventricular performance.

With an array of external transducers placed on the abdomen of a pregnant woman and recording of the fetal electrocardiograph, it should be possible to recognize and distinguish the sensor which contains the waveform of ventricular volume by ensemble-averaging or adaptive digital filtering methods. The latter techniques should eliminate maternal respiratory and cardiovascular pulsations leaving only the ventricular volume curves of the fetus. This measure would help to diagnose fetal cardiac distress by display of both electrocardiographic and ventricular volume waveform muscle abnormalities and provide early identification of fetal distress which might require obstetrical interventions.

In conjunction with the ventricular volume curve, the analysis of the thoracic aortic and the abdominal aortic pressure pulses should provide useful information on diagnosis of valvular heart disease such as aortic stenosis and a convenient non-invasive means to follow the outcome after surgical valvular repair. Thus, the upstroke of the aortic pressure curve will diminish with aortic stenosis. Abnormal aortic pressure pulses occur with stable and dissecting aneurysms of the thoracic and abdominal aorta and should help in establishing their diagnosis.

In sum, the utilization of the non-invasive method of the invention for recording ventricular volume waveforms either globally or segmentally together with analysis of aortic pressure pulses is an important advance in clinical and research cardiology. The electrocardiogram has served a highly useful purpose as an indicator of normal and abnormal electrical activity of the heartbeat, but provides no information on the mechanical responses to electrical activation. The invention described herein is the first known to continuously non-invasively monitor mechanical performance of the heart by display of segmental characteristics. It is also the first known invention to quantitatively continuously monitor changes in stroke volume. Further, the same external transducer for cardiac monitoring can be utilized to non-invasively, continuously monitor the breathing pattern. Several of the many applications that such a safe, non-invasive diagnostic tool will accomplish have been described above. Obviously, many other applications will come to mind in the future, and accordingly the above description should be construed as illustrative and not in a limiting sense, the scope of the invention being defined by the following claims.

I claim:

1. A method for monitoring cardiac function in an animal or human subject comprising:
   placing a first movement detecting transducer on the torso, said transducer overlying at least part of two diametrically opposed borders of the heart or great vessels;
   generating a signal indicative of the movement of the torso portion subtended by the transducer, said signal including a cardiac component comprising at least a sequential ventricular volume waveform or a segmental aortic pressure pulse waveform; and
   assessing cardiac function by monitoring changes in said ventricular volume waveform or said aortic pressure pulse waveform.

2. The method of claim 1, wherein said movement detecting transducer comprises a conductor disposed on said torso portion for movement therewith, movement of said torso portion resulting in corresponding changes in the self-inductance of said conductor.

3. The method of claim 2, wherein said conductor extends about said torso portion and subtends a finite height.

4. The method of claim 3, wherein said height is about 2.5 cm.

5. The method of claims 1 or 3, wherein said transducer is disposed at or near the xiphoid process and wherein said at least a segmental ventricular volume waveform or a segmental aortic pressure pulse waveform is a segmental ventricular volume waveform.

6. The method of claims 1 or 3, wherein said transducer is disposed at or near the uppermost portion of the sternum or the abdomen, and wherein said at least a segmental ventricular volume waveform or a segmental aortic pressure pulse waveform is a segmental aortic pressure pulse waveform.

7. The method of claims 1 or 3, wherein said at least a segmental ventricular volume waveform or a segmental aortic pressure pulse waveform is a segmental ventricular volume waveform, and wherein said assessing step further comprises monitoring the amplitude of said ventricular volume waveform for monitoring stroke volume.

8. The method of claims 1 or 3, wherein said assessing step further comprises monitoring changes in the slope, derivative of slope, or duration of said at least a segmental ventricular volume waveform or a segmental aortic pressure pulse waveform.

9. The method of claim 7, and further comprising monitoring the heart rate of said subject; and monitoring changes in cardiac output by monitoring changes in the product of said heart rate and said stroke volume.

10. The method of claim 9, further comprising monitoring arterial oxygen saturation; and monitoring systemic oxygen delivery ($DO_2$) trends by monitoring trends in the product of cardiac output and arterial oxygen saturation.

11. The method of claim 7, and further comprising measuring the absolute value of stroke volume by an independent method, and adjusting the level of said signal to indicate said absolute value, whereby said signal indicates absolute stroke volume.

12. The method of claim 1, wherein the step of generating a signal further comprising generating a signal having a respiration component and wherein the method for monitoring further comprises the step of removing the respiration component from said signal.

13. The method of claim 12, wherein said respiration component removing step comprises ensemble averaging said signal for removing the respiration component.

14. The method of claim 12, wherein said respiration component removing step comprises subtracting a curve fit from said signal for removing the respiration component.

15. The method of claim 12, wherein said respiration component removing step comprises adaptive digital filtering of said signal for removing the respiration component.

16. The method of claim 12, further comprising high pass filtering said signal for removing noise.

17. The method of claim 12, further comprising monitoring said respiration component.

18. The method of claim 1, further comprising performing said assessing step during breathholding for avoiding changes in said signal due to respiration.

19. The method of claim 1, further comprising placing at least one additional movement detecting transducer on the torso, said additional transducer also overlying at least part of two diametrically opposed borders of the heart or great vessels; generating a signal indicative of the movement of the torso portion subtended by said at least one additional transducer, said signal generated by said at least one additional transducer including a cardiac component comprising at least a segmental ventricular volume waveform or a segmental aortic pressure pulse waveform; and wherein said cardiac function assessing step comprises monitoring changes in said waveforms generated by said first transducer and said at least one additional transducer.

20. The method of claim 19, wherein said assessing step further comprises comparing the waveforms of said signals generated by said transducers.

21. The method of claim 19, wherein one of said movement detection transducers is selected as a reference, and further comprising the steps of determining the respiration component of the signals generated by said transducers; adjusting the amplitude of the signals generated by each additional transducer such that the respiration component of each additional movement detection transducer signal is equal to the amplitude of the respiration component of said reference transducer; and assessing cardiac function by comparing the amplitude of the cardiac component of the reference transducer signal to the amplitude of said cardiac component of at least one additional transducer signal that has been adjusted.

22. The method of claim 21, further comprising obtaining the relative amplitudes of said cardiac component of said signals generated by said transducers; repeating the steps of claim 20 on a known normal; obtaining the relative amplitudes of said cardiac component of said signals generated by said transducers when on said known normal; and comparing said relative amplitudes for said subject to said relative amplitudes for said known normal for assessing cardiac function of said subject relative to said normal.

23. The method of claims 19, 20, 21 or 22, wherein said transducers subtend an entire dimension of the heart.

24. The method of claim 23, wherein said dimension is the height of said heart from the most apical segment to the most basilar segment.

25. The method of claim 1, wherein said movement detecting transducer is a bellows pneumograph, a mercury in silastic strain gauge, an inductive circumferential transducer, a differential linear transformer, or a surface inductive plethysmograph.

26. The method of claim 1, further comprising generating an EKG signal for said subject, and wherein said assessing step further comprises monitoring changes in the timing of said at least a segmental ventricular volume waveform or a segmental aortic pressure pulse waveform relative to said EKG.

27. The method of claim 1, further comprising measuring ventriclar pressure; generating a signal indicative of ventricular pressure, wherein said at least a segmental ventricular volume waveform or a segmental aortic pressure pulse waveform is a segmental ventricular volume waveform; and constructing ventricular volume-ventricular pressure curves from said signals.

28. The method of claim 1, wherein said step of placing a first movement detecting transducer on the subject's torso comprises placing said movement detecting transducer for detecting a cardiac component of a fetus carried by said subject; and removing a respiration component and the cardiac component of said subject from said signal whereby only the cardiac component of said fetus remains in said signal.

29. The method of claim 28, further comprising removing said respiration component of said subject by monitoring during breathholding.

30. The method of claim 1, wherein said two diametrically opposed borders are the left and right borders of the heart.

31. An apparatus for monitoring cardiac function in an animal or human subject comprising:
a first movement detecting transducer means for disposition on the torso of said subject, overlying at least part of two diametrically opposed borders of the heart or great vessels;
said transducer means including means for generating a first signal indicative of the movement of the torso portions subtended by the transducer means, said first signal including a cardiac component comprising at least a segmental ventricular volume waveform or a segmental aortic pressure pulse waveform; and
means for assessing cardiac function by monitoring changes in said ventricular volume waveform or said aortic pressure pulse waveform.

32. The apparatus of claim 31, wherein said movement detecting transducer means includes a conductor for disposition on said torso portion for movement therewith, with movement of said torso portion resulting in corresponding changes in the self-inductance of said conductor.

33. The apparatus of claim 32, wherein said conductor is adapted to extend about said torso portion and subtend a finite height.

34. The apparatus of claim 33, wherein said height is about 2.5 cm.

35. The apparatus of claims 31 or 33, wherein said transducer means is adapted for disposition at or near the xiphoid process and wherein said at least a segmental ventricular volume waveform or a segmental aortic pressure pulse waveform is a segmental ventricular volume waveform.

36. The apparatus of claims 31 or 33, wherein said transducer means is adapted for disposition at or near the uppermost portion of the sternum or the abdomen, and wherein said at least a segmental ventricular volume waveform or a segmental aortic pressure pulse waveform is a segmental aortic pressure pulse waveform.

37. The apparatus of claim 31 or 33, wherein said at least a segmental ventricular volume waveform or a segmental aortic pressure pulse waveform is a segmental ventricular volume waveform, and wherein said assessing means further comprises means for monitoring the amplitude of said ventricular volume waveform for monitoring stroke volume.

38. The apparatus of claims or 31 or 33, wherein said assessing means further comprises means for monitoring changes in the slope, derivative of slope, or duration of said at least a segmental ventricular volume waveform or a segmental aortic pressure pulse waveform.

39. The apparatus of claim 37, and further comprising means for monitoring the heart rate of said subject; and means for multiplying said heart rate by stroke volume for monitoring cardiac output.

40. The apparatus of claim 39, further comprising means for monitoring arterial oxygen saturation; and means for monitoring systemic oxygen delivery ($DO_2$) trends by monitoring trends in he product of cardiac output and arterial oxygen saturation.

41. The apparatus of claim 37, and further comprising independent means for measuring the absolute value of stroke volume; and means for adjusting the level of said first signal to indicate said absolute value, whereby said first signal indicates absolute stroke volume.

42. The apparatus of claim 31, wherein the means for generating a first signal further comprises means for generating a first signal having a respiration component, and wherein the means for assessing further comprises means for removing the respiration component from said first signal.

43. The apparatus of claim 42, wherein said means for removing the respiration component from said first signal comprises means for ensemble averaging said first signal.

44. The apparatus of claim 42, wherein said means for removing the respiration component from said first signal comprises means for subtracting a curve fit from said first signal.

45. The apparatus of claim 42, wherein said means for removing the respiration component from said first signal comprises means for adaptive digital filtering said first signal.

46. The apparatus of claim 42, further comprising means for high pass filtering said first signal for removing noise.

47. The apparatus of claim 42, further comprising means for monitoring said respiration component.

48. The apparatus of claim 31, further comprising at least one additional movement detecting transducer means for disposition on said torso overlying at least part of two diametrically opposed borders of the heart or great vessels; additional means for generating an additional signal indicative of the movement of the torso portion subtended by each said at least one additional transducer means, said additional signal including a cardiac component comprising at least a segmental ventricular volume waveform or a segmental aortic pressure pulse waveform; wherein said means for assessing cardiac function comprises means for monitoring changes in said waveforms of said first and additional signals.

49. The apparatus of claim 48, wherein said assessing means further comprises means for comparing the waveforms of said first and additional signals.

50. The apparatus of claim 48, further comprising means for determining the amplitude of the respiration component of the first signal; means for adjusting each additional signal so that the amplitude of the respiration component of each additional signal is equal to the amplitude of the respiration component of said first signal, wherein said means for assessing cardiac function includes means for comparing the amplitude of the cardiac component of said first signal to the amplitude of the cardiac component of each additional signal adjusted by said means for adjusting.

51. The apparatus of claim 50, further comprising means for obtaining the relative amplitudes of said cardiac component of said first and additional signals, whereby cardiac function may be assessed by comparing said relative amplitudes for said subject to relative amplitudes obtained with a known normal.

52. The apparatus of claims 48, 49, 50 or 51, wherein said transducer means are adapted to subtend an entire dimension of the heart.

53. The apparatus of claim 52, wherein said dimension is the height of said heart from the most apical segment to the most basilar segment.

54. The apparatus of claim 48, further comprising means adapted to be worn by said subject for recording said first and additional signals for accommodating ambulatory monitoring.

55. The apparatus of claim 31, wherein said movement detecting transducer means is a bellows pneumograph, a mercury in silastic strain gauge, an inductive circumferential transducer, a differential linear transformer or a surface inductive plethysmograph.

56. The apparatus of claim 31, further comprising means for generating an EKG signal for said subject, and wherein said assessing means further comprises means for monitoring changes in the timing of said at least a segmental ventricular volume waveform or a segmental aortic pressure pulse waveform relative to said EKG.

57. The apparatus of claim 31, further comprising means for measuring ventricular pressure; means for generating a signal indicative of ventricular pressure, wherein said at least segmental ventricular volume waveform or a segmental aortic pressure pulse waveform is said at least segmental ventricular volume waveform; and means for constructing ventricular volume-ventricular pressure curves from said signals.

58. The apparatus of claim 31, wherein said movement detecting transducer means is disposed for detecting a cardiac component of a fetus carried by said subject, and further comprising means for removing a respiration component and the cardiac component of said subject from said signal whereby only the cardiac component of said fetus remains.

59. The apparatus of claim 31, further comprising means adapted to be worn by said subject for recording the first signal for accommodating ambulatory monitoring.

60. The apparatus of claim 31, wherein said two diametrically opposed borders are the left and right borders of the heart.

* * * * *